US012788799B2

(12) United States Patent
Mirsaeidi et al.

(10) Patent No.: US 12,788,799 B2
(45) **Date of Patent: *Nov. 10, 2026**

(54) METHOD OF TREATING AN INFLAMMATORY DISORDER

(71) Applicants: The University of Miami, Miami, FL (US); The United States Government as Represented by the Department of Veterans Affairs, Washington, DC (US)

(72) Inventors: Mehdi Mirsaeidi, Jacksonville, FL (US); Chongxu Zhang, Riverside, IL (US); Andrew V. Schally, Miami Beach, FL (US); Renzhi Cai, Fulshear, TX (US); Runxia Tian, Palmetto Bay, FL (US)

(73) Assignees: University of Miami, Miami, FL (US); The United States Government as Represented by the Department of Veterans Affairs, Washington, DC (US)

( * ) Notice: Subject to any disclaimer, the term of this patent is extended or adjusted under 35 U.S.C. 154(b) by 903 days.

This patent is subject to a terminal disclaimer.

(21) Appl. No.: 18/050,355

(22) Filed: Oct. 27, 2022

(65) Prior Publication Data

US 2023/0126533 A1 Apr. 27, 2023

Related U.S. Application Data

(63) Continuation of application No. PCT/US2021/029218, filed on Apr. 26, 2021.

(60) Provisional application No. 63/015,896, filed on Apr. 27, 2020.

(51) Int. Cl.

| | |
|---|---|
| ***A61K 38/25*** | (2006.01) |
| ***A61P 11/00*** | (2006.01) |
| ***A61P 29/00*** | (2006.01) |

(52) U.S. Cl.

CPC .............. *A61K 38/25* (2013.01); *A61P 11/00* (2018.01); *A61P 29/00* (2018.01)

(58) Field of Classification Search

None

See application file for complete search history.

(56) References Cited

U.S. PATENT DOCUMENTS

| | | | |
|---|---|---|---|
| 4,659,693 | A | 4/1987 | Nester |
| 4,914,189 | A | 4/1990 | Schally et al. |
| 5,084,555 | A | 1/1992 | Coy et al. |
| 5,550,212 | A | 8/1996 | Zarandi et al. |
| 5,942,489 | A | 8/1999 | Schally et al. |
| 6,057,422 | A | 5/2000 | Schally et al. |
| 6,124,263 | A | 9/2000 | Muccioli et al. |
| 7,452,865 | B2 | 11/2008 | Schally et al. |
| 8,227,405 | B2 | 7/2012 | Schally et al. |
| 8,227,421 | B2 | 7/2012 | Schally et al. |
| 8,691,942 | B2 | 4/2014 | Schally et al. |
| 9,260,504 | B2 | 2/2016 | Schally et al. |
| 2007/0042950 | A1 | 2/2007 | Schally et al. |
| 2011/0066230 | A1 | 3/2011 | Schally et al. |
| 2013/0261055 | A1 | 10/2013 | Schally et al. |
| 2014/0206836 | A1 | 7/2014 | Schally et al. |
| 2015/0166617 | A1 | 6/2015 | Schally et al. |
| 2017/0202907 | A1 | 7/2017 | Romero-Lucas |
| 2018/0250358 | A1 | 9/2018 | Schally et al. |
| 2019/0300590 | A1 | 10/2019 | Bhandari |
| 2021/0395327 | A1 | 12/2021 | Jackson et al. |
| 2022/0000983 | A1 | 1/2022 | Jackson et al. |
| 2022/0143149 | A1 | 5/2022 | Mirsaeidi et al. |

FOREIGN PATENT DOCUMENTS

| | | | |
|---|---|---|---|
| CA | 2733440 | | 2/2010 |
| CN | 1326353 | A | 12/2001 |
| CN | 102170864 | | 8/2011 |
| EP | 2222272 | | 11/2012 |
| EP | 2478011 | | 8/2014 |
| WO | 9116923 | | 11/1991 |
| WO | 9742223 | | 11/1997 |
| WO | 0031136 | | 6/2000 |
| WO | 2005016953 | | 2/2005 |
| WO | 2005113822 | | 12/2005 |
| WO | 2009120831 | | 10/2009 |
| WO | 2010015818 | | 2/2010 |
| WO | 2011034976 | | 3/2011 |
| WO | 2014004934 | | 1/2014 |
| WO | 2019060601 | | 3/2019 |
| WO | 2020163833 | | 8/2020 |
| WO | 2021011874 | | 1/2021 |
| WO | 2021222129 | | 11/2021 |

OTHER PUBLICATIONS

Salwiczek et al., Fluorinated amino acids: compatibility with native protein structures and effects on protein-protein interactions, Chem Soc Rev, 41: 2135-2171; (2012). (Year: 2012).*

Rosenkranz et al. Conjugates of Catecholamines. IV. In Vitro and in Vivo Pharmacological Activity of Monodisperse Oligopeptide Conjugates, The Journal of Pharmacology and Experimental Therapeutics, 227(2): 267-273; (1983). (Year: 1983).*

Ohshimo et al. Differential diagnosis of granulomatous lung disease: clues and pitfalls. Eur Respir Rev 2017; 26, pp. 1-16 (May 2017). (Year: 2017).*

Barabutis, Nektarios et al: "Antioxidant activity of growth hormone-releasing hormone antagonists in LNCaP human prostate cancer line," PNAS, Dec. 2008, vol. 105, No. 51:20470-20475.

Baughman, Robert P. et al: "A retrospective pilot study examining the use of Acthar gel in sarcoidosis patients," Respiratory Medicine, 2016, vol. 110:66-72.

(Continued)

*Primary Examiner* — Bridget E Bunner
*Assistant Examiner* — Regina M DeBerry
(74) *Attorney, Agent, or Firm* — Stanley A. Kim

(57) ABSTRACT

The present disclosure is directed to a method of treating an inflammatory disorder, such as sarcoidosis, using a growth hormone-releasing hormone (GHRH) antagonist.

3 Claims, 9 Drawing Sheets

Specification includes a Sequence Listing.

(56) References Cited

OTHER PUBLICATIONS

Baughman, Robert P. et al: "Clinical characteristics of patients in a case control study of sarcoidosis," Am J Respir Crit Care Med, 2001, vol. 164:1885-1889.
Brownell, Isaac et al: "Evidence for mycobacteria in sarcoidosis," Am J Respir Cell Mol Biol, 2011, vol. 45:899-905.
Auerbach, Robert et al: "Angiogenesis assays: Problems and pitfalls," Cancer and Metastasis Review, 2000, vol. 19:167-172.
Cervini, Laura A. et al:"Human Growth Hormone-Releasing Hormone hGHRH(1-29)-NH2: Systematic Structure-Activity Relationship Studies," J. Med. Chem, 1998, vol. 41: 717-727.
Dermer, Gerald B.: "Another Anniversary for the War on Cancer," Biotechnology, 1994, vol. 12: 320.
Gura, Trisha: "Systems for Identifying New Drugs are Often Faulty," Science, 1997, vol. 278, Issue 5340: 1041-1042.
Halmos, Gabor et al.: "Human renal cell carcinoma expresses distinct binding sites for growth hormone-releasing hormone," PNAS, Sep. 2000, vol. 97, No. 19: 10555-10560.
Jaffe, Craig A. et al.: "Suppression of growth hormone (GH) hypersecretion due to Ectopic GH-releasing hormne (GHRH) by a selective GHRH antagonist," Journal of Clinical Endocrinology and Metabolism, 1996, vol. 82, No. 2: 634-637.
Jain, Rakesh K. et al: "Quantitative angiogenesis assays: Progress and problems," Nature Medicine, 1997, vol. 3, No. 11: 1203-1208.
Kiaris, Hippokratis et al: "Expression of a splice variant of the receptor for GHRH in 3T3 fibroblasts activates cell proliferation responses to GHRH analogs," PNAS, Jan. 2002, vol. 99, No. 1: 196-200.
Klukovits, Anna et al.: "Novel antagonists of growth hormone-releasing hormone inhibit growth and vascularization of human experimental ovarian cancers," Cancer, 2012: 670-680.
Letsch, Markus et a.: "Growth hormone-releasing hormone (GHRH) antagonists inhibit the proliferation of androgen-dependent and-independent prostate cancers," PNAS, Feb. 2003, vol. 100, No. 3: 1250-1255.
Merrifield, R.B.: Solid phase peptide synthesis. I. The synthesis of a tetrapeptide, Syntheisis of a Tetrapeptide, Jul. 1963, vol. 85: 2149-2154.
Perez, Roberto et al.: "Antagonists of growth hormone-releasing hormone suppress in vivo tumor growth and gene expression in triple negative breast cancers," Oncotarget, 2012, vol. 3: 988-997.
Plonowski, Artur et al.: "Inhibition of proliferation of PC-3 human prostrate cancer by antagonists of growth hormone-releasing hormone: Lack of correlation with the levels of serum IGF-I and expression of Tumoral IGF-II and vascular endothelial growth factor," The Prostrate, 2002, vol. 52: 173-182.
Pozsgai, Eva et al.: "The effect of GHRH antagonists on human glioblastomas and their mechanism of action," Int. J. Cancer, 2010, vol. 127: 2313-2322.
Pozsgai, Eva et al.: "The effect of a novel antagonist of growth hormone releasing hormone on cell proliferation and on the key cell signaling pathways in nine different breast cancer cell lines," Int Journal of Oncology, 2011, vol. 39: 1025-1032.
Rekasi, Zoltan et al.: "Antagonists of growth hormone-releasing hormone and vasoactive intestinal peptide inhibit tumor proliferation by different mechanisms: Evidence from in vitro studies on human prostatic and pancreatic cancers," Endocrinology, 2000, vol. 141, No. 6: 2120-2128.
Rekasi, Zoltan et al.: "Islolation and sequencing of cDNAs for splice variants of growth hormone-releasing hormone receptors from human cancers," PNAS, Sep. 2000, vol. 97, No. 19: 10561-10566.
Schally, Andrew V. et al.: "Antagonistic analogs of growth hormone-releasing hormone: New potential antitumor agents," TEM, 1999, vol. 10, No. 10: 383-391.
Schally, Andrew V. et al.: "Hypothalamic hormones and cancer," Frontiers in Neuroendocrinology, 2002, vol. 22: 248-291.
Schally, Andrew V. et al.: "Antagonists of growth hormone-releasing hormone in oncology," Combinatorial Chemistry & High Throughput Screening, 2006, vol. 9: 163-170.
Siejka, A. et al.: "GH-RH antagonist (MZ-4-71) inhibits VEGF secretion and proliferation of murine endothelial cells," Life Sciences, 2003, vol. 72: 2473-2479.
Szepeshazi, Karoly et al.: "Antagonists of GHRH decrease production of GH and IGF-I in MXT mouse mammary cancers and inhibit tumor growth," Endocrinology, 2001, vol. 14: 4371-4378.
Szereday, Zoltan et al.: "Antagonists of growth hormone-releasing hormone inhibit the proliferation of experimental non-small cell lung carcinoma," Cancer Research, 2003, vol. 63: 7913-7919.
Toth, Katalin et al.: "New analogs of human growth hormone-releasing hormone (1-29) with high and prolonged antagonistic activity," J. Peptide Res., 1998, vol. 51: 134-141.
Varga, Jozsef L. et al.: "Synthesis and biological evaluation of antagonists of growth hormone-releasing hormone with high and protracted in vivo activities," Proc. Natl. Acad. Sci., 1999, vol. 96: 692-697.
Varga, Jozsef L. et al.: "Increased activity of antagonists of growth hormone-releasing hormone substituted at positions 8, 9, and 10," PNAS, Feb. 2004, vol. 101, No. 6: 1708-1713.
Voskoglou-Nomikos, Theodora et al.: "Clinical predictive value of the in vitro cell line, human xenograft, and mouse allograft preclinical cancer models," Clinical Cancer Research, 2003, vol. 9: 4227-4239.
Zarandi, Marta et al.: "Potent agonists of growth hormone-releasing hormone," Int. J. Peptide Protein Res., 1992, vol. 39: 211-217.
Zarandi, M. et al.: "Synthesis and biological activities of highly potent antagonists of growth hormone-releasing hormone," Proc. Natl. Acad. Sci., 1994 vol. 91: 12298-12302.
"Restenosis Treatment," web page ,<https://www/news-medical.net/health/Restenosis-Treatment.aspx>, 7 pages, retrieved from website on Mar. 18, 2022.
Cabrera, Sandra et al.: "Gene expression profiles reveal molecular mechanisms involved in the progression and resolution of bleomycin-induced lung fibrosis," Am J Physiol Lung Cell Mol Physiol, 2013, vol. 304: 593-601.
Chen, Edward S. et al.: "Etiology of sarcoidosis," Clin Chest Med, 2008, vol. 29: 365-377.
Cui, Tengjiao et al.: "Agonistic analogs of growth hormone releasing hormone (GHRH) promote wound healing by stimulating the proliferation and survival of human dermal fibroblasts through ERK and AKT pathways," Aug. 2016, Oncotarget, vol. 7, No. 33: 52661-52672.
Dubaniewicz, Anna et al.: "*Mycobacterium tuberculosis* complex and mycobacterial heat shock proteins in lymph hode tissue from patient with pulmonary sarcoidosis," Journal of Clinical Microbiology, 2006, vol. 44, No. 9: 3448-3451.
Elhai, Muriel et al.: "OX40L blockade protects against inflammation-driven fibrosis," PNAS, Jun. 2016: E3901-E3910.
Facchetti, Fabio et al.: "Expression of Inducible nitric oxide synthase in human granulomas and histiocytic reactions," American Journal of Pathology, Jan. 1999, vol. 154, No. 1: 145-152.
Fu, Yung-Kang et al.: "A novel role of growth hormone and insulin-like growth factor-1," The Journal of Immunology, 1991 vol. 146: 1602-1608.
Havt, Alexandre et al.: "The expression of the pituitary growth hormone-releasing hormone receptor and its splice variants in normal and neoplastic human tissues," PNAS, Nov. 2005, vol. 102, No. 48: 17424-17429.
Huang, Xinqiang et al.: "Molecular characterization of a precision-cut rat lung slice model for the evaluation of antifibrotic drugs," Am J Physiol Lung Cell Mol Physiol, 2019, vol. 316: L348-L357.
Jenkins, R. Gisli et al.: "An official american thoracic society workshop report: Use of animal models for the preclinical assessment of potential therapies for pulmonary fibrosis," Am J Respir Cell Mol Biol, 2017, vol. 56, No. 5: 667-679.
Koh, Timothy J. et al.: "Inflammation and wound healing: the role of the macrophage," Expert Review in Molecular Medcine, Jul. 2011, vol. 13, e23: 1-12.
Kral, Julia Barbara et al.: "Sustained PI3K Activation exaerbates BLM-induced lung fibrosis via activation of pro-inflammatory and pro-fibrotic pathways," Scientific Reports, Mar. 2016, pp. 1-16.

(56) References Cited

OTHER PUBLICATIONS

Kucera, Gena P. et al: "Occupational risk factors for sarcoidosis in African-American siblings," Chest, May 2003, vol. 5: 1527-1535.
Lazarus, Angeline: "Sarcoidosis: Epidemiology, etiology, pathogenesis, and genetics," DM, Nov. 2009: 649-660.
Miller, Milton A. et al.: "Effect of acthar-c (ACTH) in sarcoidosis," Case Reports, Feb. 1952:776-784.
Mirsaeidi, Mehdi et al.: "Racial difference in sarcoidosis mortality in the United States," Chest, Feb. 2015, vol. 147, No. 2: 438-449.
Jackson, Robert M. et al.: "Growth hormone-releasing hormone receptor antagonist MIA-602 modulates mouse lung inflammation and fibrosis due to bleomycin," European Respiratory journal, 2018, 52 Suppl. 62:1-2; (Only Abstract—No Full-Text Version is Available).
Cleveland Clinic: Pulmonary Fibrosis, <https://my.clevelandclinic.org/health/diseases/10959-pulmonary-fibrosis#symptoms-and-causes>, accessed online on Jul. 26, 2023.
Qin, Yong Jie et al., "Antagonist of GH-releasing hormone receptors alleviates experimental ocular inflammation," PNAS, 2014, vol. 111, No. 51:18303-18308.
Kono, Keiko, "Eye Lesion of Sarcoidosis, the Therapy and Adult Disease," Lifestyle-Related Disease, 2023, 43rd vol., No. 10:1229-1233.
Newman, Lee S. et al.: "A case control etiologic study of sarcoidosis," Am J Respir Crit Care Med, 2004, vol. 170: 1324-1330.
Nunes, Hilario et al.: Sarcoidosis, Orphanet Journal of Rare Diseases, 2007, vol. 2, No. 46: 1-8.
Ocampo-Lin, Blanca et al.: "Nocturnal growth hormone (GH) secretion is eliminated by infusion of GH-releasing hormone antagonist," Journal of Clinical Endocrinology and Metabolism, 1996, vol. 81, No. 12: 4396-4399.
Oswald-Richter, Kyra A. et al.: "Dual analysis for mycobacteria and propionibacteria in sarcoidosis BAL," J Clin Immunol, 2012, vol. 32: 1129-1140.
Patterson, Karen C. et al.: "Pulmonary fibrosis in sarcoidosis," Ann Am Thorac Soc, Aug. 2013, vol. 10, No. 4: 362-370.
Ren, Jia Lin et al.: "Growth hormone-releasing hormone receptor mediates cytokine production in ciliary and iris epithelial cells during LPS-induced ocular inflammation," Experimental Eye Research, 2019, vol. 181: 277-284.
Ryter Stefan W. et al.: "Mitochondrial dysfunction as a pathogenic mediator of chronic obstructive pulmonary disease and idiopathic pulmonary fibrosis," Ann Am Thorac Soc, Dec. 2018, vol. 15, Supplement 4: S266-S272.
Hung, Chi F. et al: "Role of IGF-1 pathway in lung fibroblast activation," Respiratory Research, 2013, vol. 14: 1-.
Schally, Andrew V. et al.: "Hypothalamic and other peptide hormones," Endocrine Therapy, 2003, Section 14: 911-926.
Simonian, Philip L. et al.: "Regulatory role of γδ T cells in the recruitment of CD4+ and CD8+ T cells to lung and subsequent pulmonary fibrosis," The Journal of Immunology, 2006, vol. 177: 4436-4443.
Bellyei, Szabolcs et al.: "GHRH antagonists reduce the invasive and metastatic potential of human cancer cell lines in vitro," Cancer Letters, 2010, vol. 293: 31-40.
Warwick-Davies, Jan et al.: "Growth hormone is a human macrophage activating factor," The Journal of Immunology, 1995, vol. 154: 1909-1918.
Waters, David W. et al.: "STAT3 regulates the onset of oxidant-induced senescence in lung fibroblasts," Am J Respir Cell Mol Biol, 2019, vol. 61, Issue No. 1: 61-73.
Zarandi, Marta et al.: "Synthesis and structure-activity studies on novel analogs of human growth hormone releasing hormone (GHRH) with enhanced inhibitory activities on tumor growth," Peptides, 2017, vol. 89: 60-70.
Zhang, Chongxu et al.: "Growth hormone-releasing hormone receptor antagonist modulates lung inflammation and fibrosis due to bleomycin," Lung, 2019, vol. 197: 541-549.
Chen, Edward et al.: "Serum amyloid A regulates granulomatous inflammation in sarcoidosis through toll-like receptor-2," Am J Respir Crit Care Med, 2010, vol. 181: 360-373.
Gan, Jinfeng et al.: Growth hormone-releasing hormone receptor antagonists inhibit human gastric cancer through downregulation of PAK1-STAT3/NF-κB signaling, PNAS, 2016, vol. 113, No. 51: 14745-14550.
Rutherford, Robert et al.: "Mycobacteria in Pathogenesis of Sarcoidosis," Chest., 2004; 125(1):354.
Fang, Chuling, et al.: "Immunological Evidence for the Role of Mycobacteria in Sarcoidosis: A Meta-Analysis," PLOS ONE, 2016, No. 10:1-14.
Iannuzzi, Michael C. et al: "Sarcoidosis," The New England Journal of Medicine, 2007, No. 357:2153-2165.

* cited by examiner

| | 0 | 6 | 8 | 9 | 10 | 11 | 12 | 20 | 21 | 29 | 30 | MW | MW-TFA |
|---|---|---|---|---|---|---|---|---|---|---|---|---|---|
| MIA-602 | PhAC-Ada | 5FPhe | Ala | - | - | His | Orn | His | Orn | Har-$NH_2$ | | 3931 | 4843 |
| MIA-690 | - | Cpa | - | - | 5FPhe | - | - | - | - | - | | 3934 | 4846 |
| AVR-235 | 5FPhAC-Ada | 5FPhe | - | - | Tyr(Me) | Arg | Lys | Arg | Lys | Har-$NHCH_3$ | | 4101 | 5013 |
| AVR-333 | - | Cpa | Asn | - | - | - | - | - | - | Har | Ada-$NH_2$ | 4271 | 5183 |
| AVR-352 | - | 5FPhe | Ala | - | - | - | - | - | - | Har | Ada-$NH_2$ | 4284 | 5196 |
| AVR-353 | - | Cpa | - | - | 5FPhe | - | - | - | - | Har | Ada-$NH_2$ | 4287 | 5199 |
| AVR-354 | - | - | - | - | - | - | - | - | - | Har | Ada-$NHCH_3$ | 4301 | 5213 |

*FIG. 7*

FIG. 8

| SEQ ID NO: | | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | MW | MW-TFA |
|---|---|---|---|---|---|---|---|---|---|---|---|---|---|---|---|---|---|---|---|---|---|---|---|---|---|---|---|---|---|---|---|---|---|---|
| 22 | MIA-602 | PhAC-Ada | Tyr | D-Arg | Asp | Ala | Ile | 5FPhe | Thr | Ala | Har | Tyr(Me) | His | Orn | Val | Leu | Abu | Gln | Leu | Ser | Ala | His | Orn | Leu | Leu | Gln | Asp | Ile | Nle | D-Arg | Har-$NH_2$ | | 3928 | 4840 |
| 23 | MIA-690 | PhAC-Ada | Tyr | D-Arg | Asp | Ala | Ile | Cpa | Thr | Ala | Har | 5FPhe | His | Orn | Val | Leu | Abu | Gln | Leu | Ser | Ala | His | Orn | Leu | Leu | Gln | Asp | Ile | Nle | D-Arg | Har-$NH_2$ | | 3931 | 4843 |
| 8 | **AVR-104** | PhAC-Ada | Tyr | D-Arg | Asp | Ala | Ile | Cpa | Thr | Ala | Arg | Tyr(Me) | Arg | Lys | Val | Leu | Abu | Gln | Leu | Ser | Ala | His | Orn | Leu | Leu | Gln | Asp | Ile | Nle | D-Arg | Har-$NH_2$ | | 3891 | 4803 |
| 9 | **AVR107** | PhAC-Ada | Tyr | D-Arg | Asp | Ala | Ile | Cpa | Thr | Ala | Arg | Tyr | Arg | Lys | Val | Leu | Abu | Gln | Leu | Ser | Ala | Arg | Lys | Leu | Leu | Gln | Asp | Ile | Nle | D-Arg | Har-$NH_2$ | | 3909 | 4821 |
| 10 | **AVR-116** | PhAC-Ada | Tyr | D-Arg | Asp | Ala | Ile | Cpa | Thr | Ala | Arg | 5FPhe | Arg | Lys | Val | Leu | Abu | Gln | Leu | Ser | Ala | His | Orn | Leu | Leu | Gln | Asp | Ile | Nle | D-Arg | Har-$NH_2$ | | 3950 | 4862 |
| 11 | **AVR-120** | D-Phe-Ada | Tyr | D-Arg | Asp | Ala | Ile | Cpa | Thr | Ala | Arg | Tyr(Me) | Arg | Lys | Val | Leu | Abu | Gln | Leu | Ser | Ala | His | Orn | Leu | Leu | Gln | Asp | Ile | Nle | D-Arg | Har-$NH_2$ | | 3919 | 4831 |
| 12 | **AVR-201** | PhAC-Ada | Tyr | D-Arg | Asp | Ala | Ile | Cpa | Thr | Ala | Arg | Amp | Arg | Lys | Val | Leu | Abu | Gln | Leu | Ser | Ala | His | Orn | Leu | Leu | Gln | Asp | Ile | Nle | D-Arg | Har-$NHCH_3$ | | 3889 | 4801 |
| 13 | **AVR-234** | PhAC-Ada | Tyr | D-Arg | Asp | Ala | Ile | Cpa | Thr | Asn | Arg | Tyr(Me) | Arg | Lys | Val | Leu | Abu | Gln | Leu | Ser | Ala | Arg | Lys | Leu | Leu | Gln | Asp | Ile | Nle | D-Arg | Har-$NHCH_3$ | | 3981 | 4893 |
| 3 | **AVR-235** | 5FPhAC-Ada | Tyr | D-Arg | Asp | Ala | Ile | 5FPhe | Thr | Ala | Har | Tyr(Me) | Arg | Lys | Val | Leu | Abu | Gln | Leu | Ser | Ala | Arg | Lys | Leu | Leu | Gln | Asp | Ile | Nle | D-Arg | Har-$NHCH_3$ | | 4098 | 5010 |
| 14 | **AVR-321** | PhAC-Ada | Tyr | D-Arg | Asp | Ala | Ile | Cpa | Thr | Asn | Har | Tyr(Me) | Arg | Lys | Val | Leu | Abu | Gln | Leu | Ser | Ala | Arg | Lys | Leu | Leu | Gln | Asp | Ile | Nle | D-Arg | Har | Aoc-$NHCH_3$ | 4136 | 5048 |
| 15 | **AVR-322** | 5FPhAC-Ada | Tyr | D-Arg | Asp | Ala | Ile | Cpa | Thr | Asn | Har | Tyr(Me) | Arg | Lys | Val | Leu | Abu | Gln | Leu | Ser | Ala | Arg | Lys | Leu | Leu | Gln | Asp | Ile | Nle | D-Arg | Har | Aoc-$NHCH_3$ | 4226 | 5138 |
| 24 | **AVR-332** | PhAC-Ada | Tyr | D-Arg | Asp | Ala | Ile | Cpa | Thr | Asn | Har | Tyr(Me) | Arg | Lys | Val | Leu | Abu | Gln | Leu | Ser | Ala | Arg | Lys | Leu | Leu | Gln | Asp | Ile | Nle | D-Arg | Har | Ada-$NH_2$ | 4176 | 5090 |
| 4 | **AVR-333** | 5FPhAC-Ada | Tyr | D-Arg | Asp | Ala | Ile | Cpa | Thr | Asn | Har | Tyr(Me) | Arg | Lys | Val | Leu | Abu | Gln | Leu | Ser | Ala | Arg | Lys | Leu | Leu | Gln | Asp | Ile | Nle | D-Arg | Har | Ada-$NH_2$ | 4268 | 5180 |
| 5 | **AVR-352** | 5FPhAC-Ada | Tyr | D-Arg | Asp | Ala | Ile | 5FPhe | Thr | Ala | Har | Tyr(Me) | Arg | Lys | Val | Leu | Abu | Gln | Leu | Ser | Ala | Arg | Lys | Leu | Leu | Gln | Asp | Ile | Nle | D-Arg | Har | Ada-$NH_2$ | 4281 | 5193 |
| 6 | **AVR-353** | 5FPhAC-Ada | Tyr | D-Arg | Asp | Ala | Ile | Cpa | Thr | Ala | Har | 5FPhe | Arg | Lys | Val | Leu | Abu | Gln | Leu | Ser | Ala | Arg | Lys | Leu | Leu | Gln | Asp | Ile | Nle | D-Arg | Har | Ada-$NH_2$ | 4284 | 5196 |
| 7 | **AVR-354** | 5FPhAC-Ada | Tyr | D-Arg | Asp | Ala | Ile | Cpa | Thr | Ala | Har | 5FPhe | Arg | Lys | Val | Leu | Abu | Gln | Leu | Ser | Ala | Arg | Lys | Leu | Leu | Gln | Asp | Ile | Nle | D-Arg | Har | Ada-$NHCH_3$ | 4296 | 5210 |
| 16 | **AVR-542** | 5FPhAC-Ada | Tyr | D-Arg | Asp | Ala | Ile | Cpa | Thr | Ala | Har | 5FPhe | His | Orn | Val | Leu | Abu | Gln | Leu | Ser | Ala | His | Orn | Leu | Leu | Gln | Asp | Ile | Nle | D-Arg | Har-$NHCH_3$ | | 4038 | 4950 |
| 17 | **AVR-543** | 5FPhAC-Ada | Tyr | D-Arg | Asp | Ala | Ile | Cpa | Thr | Ala | Har | 5FPhe | His | Orn | Val | Leu | Abu | Gln | Leu | Ser | Ala | His | Orn | Leu | Leu | Gln | Asp | Ile | Nle | D-Arg | Har | Ada-$NHCH_3$ | 4232 | 5144 |
| 18 | **AVR-552** | 5FPhAC-Ada | Tyr | D-Arg | Asp | Ala | Ile | Cpa | Thr | Ala | Har | 5FPhe | His | Orn | Val | Leu | Abu | Gln | Leu | Ser | Ala | His | Orn | Leu | Leu | Gln | Asp | Ile | Nle | D-Arg | Har | Ada-$NH_2$ | 4218 | 5130 |
| 19 | **AVR-553** | 5FPhAC-Ada | Tyr | D-Arg | Asp | Ala | Ile | 5FPhe | Thr | Ala | Har | Tyr(Me) | His | Orn | Val | Leu | Abu | Gln | Leu | Ser | Ala | His | Orn | Leu | Leu | Gln | Asp | Ile | Nle | D-Arg | Har | Ada-$NH_2$ | 4215 | 5127 |
| 20 | **AVR-620** | 5FPhAC-Ada | Tyr | D-Arg | Asp | Ala | Ile | Cpa | Thr | Asn | Arg | Tyr(Me) | Arg | Lys | Val | Leu | Abu | Gln | Leu | Ser | Ala | His | Orn | Leu | Leu | Gln | Asp | Ile | Nle | D-Arg | Har | Ada-$NH_2$ | 4224 | 5136 |

SEQUENCE LISTING

```
Sequence total quantity: 26
SEQ ID NO: 1            moltype = AA  length = 29
FEATURE                 Location/Qualifiers
source                  1..29
                        mol_type = protein
                        organism = synthetic construct
                        note = Synthetic Polypeptide
VARIANT                 1
                        note = MISC_FEATURE - 5FPhAC-Ada, p-ClPhAC, D-Phe-Ada, or
                         PhAC-Ada - pentafluoro-phenylacetyl-12-aminododecanoic
                         acid tyrosine, para-chlorophenylacetic acid tyrosine,
                         D-phenylalanine-aminododecanoic acid tyrosine, or
                         phenylacetyl-12-aminododecanoic acid tyrosine
SITE                    2
                        note = MISC_FEATURE - DArg - D-arginine
VARIANT                 6
                        note = MISC_FEATURE - 5FPhe or Cpa -
                         pentafluoro-phenylalanine or para-choloro-phenylalanine
VARIANT                 8
                        note = MISC_FEATURE - Ala or Asn
VARIANT                 9
                        note = MISC_FEATURE - Arg or Har - Arginine or Homoarginine
VARIANT                 10
                        note = MISC_FEATURE - Tyr(Me), Amp or 5FPhe -
                         O-methyl-tyrosine, para-amino-phenylalanine, or
                         pentafluoro-phenylalanine
VARIANT                 11
                        note = MISC_FEATURE - Arg or His
VARIANT                 12
                        note = MISC_FEATURE - Lys or Orn - Lys or Ornithine
```

```
SITE                    15
                        note = MISC_FEATURE - Abu - alpha-aminobutyric acid
VARIANT                 20
                        note = MISC_FEATURE - Arg or His
VARIANT                 21
                        note = MISC_FEATURE - Lys or Orn - Lys or Ornithine
SITE                    27
                        note = MISC_FEATURE - Nle - norleucine
SITE                    28
                        note = MISC_FEATURE - DArg - D-arginine
VARIANT                 29
                        note = MISC_FEATURE - Har, Har-NH2 or Har-NHCH3 -
                         MISC_FEATURE - present or absent and, when present, is
                         Ada-NH2, Ada-NHCH or Ada-NHCH2CH3, or a pharmaceutically
                         acceptable salt thereof - Homoarginine,
                         homoarginine-amide, or homoarginine-methylamine which may
                         be attached to 12-aminododecanoic acid amide,
                         12-aminododecanoic acid methylamine, 12-aminododecanoic
                         acid ethylamine, or a pharmaceutically acceptable salt
                         thereof
SEQUENCE: 1
YRDAIXTXXX XXVLXQLSAX XLLQDIXRX                                    29

SEQ ID NO: 2            moltype = AA  length = 29
FEATURE                 Location/Qualifiers
source                  1..29
                        mol_type = protein
                        organism = synthetic construct
                        note = Synthetic Polypeptide
SITE                    1
                        note = MISC_FEATURE - 5FPhAC-Ada -
                         pentafluoro-phenylacetyl-12-aminododecanoic acid tyrosine
SITE                    2
                        note = MISC_FEATURE - DArg - D-arginine
VARIANT                 6
                        note = MISC_FEATURE - 5FPhe or Cpa -
                         pentafluoro-phenylalanine or para-choloro-phenylalanine
VARIANT                 8
                        note = MISC_FEATURE - Ala or Asn
SITE                    9
                        note = MISC_FEATURE - Har - Homoarginine
VARIANT                 10
                        note = MISC_FEATURE - Tyr(Me) or 5FPhe - O-methyl-tyrosine
                         or pentafluoro-phenylalanine
SITE                    15
                        note = MISC_FEATURE - Abu - alpha-aminobutyric acid
SITE                    27
                        note = MISC_FEATURE - Nle - norleucine
SITE                    28
                        note = MISC_FEATURE - DArg - D-arginine
VARIANT                 29
                        note = MISC_FEATURE - Har or Har-NHCH3 - MISC_FEATURE -
                         present or absent and, when present, is Ada-NH2 or
                         Ada-NHCH3, or a pharmaceutically acceptable salt thereof -
                         Homoarginine or homoarginine-methylamine which may be
                         attached to 12-aminododecanoic acid amide,
                         12-aminododecanoic acid methylamine, or a pharmaceutically
                         acceptable salt thereof
SEQUENCE: 2
YRDAIXTXXX RKVLXQLSAR KLLQDIXRX                                    29

SEQ ID NO: 3            moltype = AA  length = 28
FEATURE                 Location/Qualifiers
source                  1..28
                        mol_type = protein
                        organism = synthetic construct
                        note = Synthetic Polypeptide
SITE                    1
                        note = MISC_FEATURE - 5FPhAC-Ada -
                         pentafluoro-phenylacetyl-12-aminododecanoic acid tyrosine
SITE                    2
                        note = MISC_FEATURE - DArg - D-arginine
SITE                    6
                        note = MISC_FEATURE - 5FPhe - pentafluoro-phenylalanine
SITE                    9
                        note = MISC_FEATURE - Har - Homoarginine
SITE                    10
                        note = MISC_FEATURE - Tyr(Me) - O-methyl-tyrosine
SITE                    15
```

```
                        note = MISC_FEATURE - Abu - alpha-aminobutyric acid
SITE                    27
                        note = MISC_FEATURE - Nle - norleucine
SITE                    28
                        note = MISC_FEATURE - DArg-NHCH3 - D-arginine-methylamine
SEQUENCE: 3
YRDAIFTAXY RKVLXQLSAR KLLQDIXR                                      28

SEQ ID NO: 4            moltype = AA  length = 29
FEATURE                 Location/Qualifiers
source                  1..29
                        mol_type = protein
                        organism = synthetic construct
                        note = Synthetic Polypeptide
SITE                    1
                        note = MISC_FEATURE - 5FPhAC-Ada -
                         pentafluoro-phenylacetyl-12-aminododecanoic acid tyrosine
SITE                    2
                        note = MISC_FEATURE - DArg - D-arginine
SITE                    6
                        note = MISC_FEATURE - Cpa - para-chloro-phenylalanine
SITE                    9
                        note = MISC_FEATURE - Har - Homoarginine
SITE                    10
                        note = MISC_FEATURE - Tyr(Me) - O-methyl-tyrosine
SITE                    15
                        note = MISC_FEATURE - Abu - alpha-aminobutyric acid
SITE                    27
                        note = MISC_FEATURE - Nle - norleucine
SITE                    28
                        note = MISC_FEATURE - DArg - D-arginine
SITE                    29
                        note = MISC_FEATURE - Har-Ada-NH2 -
                         Homoarginine-12-aminododecanoic acid amide
SEQUENCE: 4
YRDAIFTNXY RKVLXQLSAR KLLQDIXRX                                     29

SEQ ID NO: 5            moltype = AA  length = 29
FEATURE                 Location/Qualifiers
source                  1..29
                        mol_type = protein
                        organism = synthetic construct
                        note = Synthetic Polypeptide
SITE                    1
                        note = MISC_FEATURE - 5FPhAC-Ada -
                         pentafluoro-phenylacetyl-12-aminododecanoic acid tyrosine
SITE                    2
                        note = MISC_FEATURE - DArg - D-arginine
SITE                    6
                        note = MISC_FEATURE - 5FPhe - pentafluoro-phenylalanine
SITE                    9
                        note = MISC_FEATURE - Har - Homoarginine
SITE                    10
                        note = MISC_FEATURE - Tyr(Me) - O-methyl-tyrosine
SITE                    15
                        note = MISC_FEATURE - Abu - alpha-aminobutyric acid
SITE                    27
                        note = MISC_FEATURE - Nle - norleucine
SITE                    28
                        note = MISC_FEATURE - DArg - D-arginine
SITE                    29
                        note = MISC_FEATURE - Har-Ada-NH2 -
                         Homoarginine-12-aminododecanoic acid amide
SEQUENCE: 5
YRDAIFTAXY RKVLXQLSAR KLLQDIXRX                                     29

SEQ ID NO: 6            moltype = AA  length = 29
FEATURE                 Location/Qualifiers
source                  1..29
                        mol_type = protein
                        organism = synthetic construct
                        note = Synthetic Polypeptide
SITE                    1
                        note = MISC_FEATURE - 5FPhAC-Ada -
                         pentafluoro-phenylacetyl-12-aminododecanoic acid tyrosine
SITE                    2
                        note = MISC_FEATURE - DArg - D-arginine
SITE                    6
                        note = MISC_FEATURE - Cpa - para-chloro-phenylalanine
```

```
SITE                  9
                      note = MISC_FEATURE - Har - Homoarginine
SITE                  10
                      note = MISC_FEATURE - 5FPhe - pentafluoro-phenylalanine
SITE                  15
                      note = MISC_FEATURE - Abu - alpha-aminobutyric acid
SITE                  27
                      note = MISC_FEATURE - Nle - norleucine
SITE                  28
                      note = MISC_FEATURE - DArg - D-arginine
SITE                  29
                      note = MISC_FEATURE - Har-Ada-NH2 -
                       Homoarginine-12-aminododecanoic acid amide
SEQUENCE: 6
YRDAIFTAXF RKVLXQLSAR KLLQDIXRX                                   29

SEQ ID NO: 7          moltype = AA  length = 29
FEATURE               Location/Qualifiers
source                1..29
                      mol_type = protein
                      organism = synthetic construct
                      note = Synthetic Polypeptide
SITE                  1
                      note = MISC_FEATURE - 5FPhAC-Ada -
                       pentafluoro-phenylacetyl-12-aminododecanoic acid tyrosine
SITE                  2
                      note = MISC_FEATURE - DArg - D-arginine
SITE                  6
                      note = MISC_FEATURE - Cpa - para-chloro-phenylalanine
SITE                  9
                      note = MISC_FEATURE - Har - Homoarginine
SITE                  10
                      note = MISC_FEATURE - 5FPhe - pentafluoro-phenylalanine
SITE                  15
                      note = MISC_FEATURE - Abu - alpha-aminobutyric acid
SITE                  27
                      note = MISC_FEATURE - Nle - norleucine
SITE                  28
                      note = MISC_FEATURE - DArg - D-arginine
SITE                  29
                      note = MISC_FEATURE - Har-Ada-NHCH3 -
                       Homoarginine-12-aminododecanoic acid methylamine
SEQUENCE: 7
YRDAIFTAXF RKVLXQLSAR KLLQDIXRX                                   29

SEQ ID NO: 8          moltype = AA  length = 29
FEATURE               Location/Qualifiers
source                1..29
                      mol_type = protein
                      organism = synthetic construct
                      note = Synthetic Polypeptide
SITE                  1
                      note = MISC_FEATURE - PhAC-Ada -
                       phenylacetyl-12-aminododecanoic acid tyrosine
SITE                  2
                      note = MISC_FEATURE - DArg - D-arginine
SITE                  6
                      note = MISC_FEATURE - Cpa - para-chloro-phenylalanine
SITE                  10
                      note = MISC_FEATURE - Tyr(Me) - O-methyl-tyrosine
SITE                  15
                      note = MISC_FEATURE - Abu - alpha-aminobutyric acid
SITE                  21
                      note = MISC_FEATURE - Orn - Ornithine
SITE                  27
                      note = MISC_FEATURE - Nle - norleucine
SITE                  28
                      note = MISC_FEATURE - DArg - D-arginine
SITE                  29
                      note = MISC_FEATURE - Har-NH2 - Homoarginine-amide
SEQUENCE: 8
YRDAIFTARY RKVLXQLSAH XLLQDIXRX                                   29

SEQ ID NO: 9          moltype = AA  length = 29
FEATURE               Location/Qualifiers
source                1..29
                      mol_type = protein
                      organism = synthetic construct
                      note = Synthetic Polypeptide
```

-continued

```
SITE                   1
                       note = MISC_FEATURE - PhAC-Ada -
                        phenylacetyl-12-aminododecanoic acid tyrosine
SITE                   2
                       note = MISC_FEATURE - DArg - D-arginine
SITE                   6
                       note = MISC_FEATURE - Cpa - para-chloro-phenylalanine
SITE                   15
                       note = MISC_FEATURE - Abu - alpha-aminobutyric acid
SITE                   27
                       note = MISC_FEATURE - Nle - norleucine
SITE                   28
                       note = MISC_FEATURE - DArg - D-arginine
SITE                   29
                       note = MISC_FEATURE - Har-NH2 - Homoarginine-amide
SEQUENCE: 9
YRDAIFTARY RKVLXQLSAR KLLQDIXRX                                    29

SEQ ID NO: 10          moltype = AA  length = 29
FEATURE                Location/Qualifiers
source                 1..29
                       mol_type = protein
                       organism = synthetic construct
                       note = Synthetic Polypeptide
SITE                   1
                       note = MISC_FEATURE - PhAC-Ada -
                        phenylacetyl-12-aminododecanoic acid tyrosine
SITE                   2
                       note = MISC_FEATURE - DArg - D-arginine
SITE                   6
                       note = MISC_FEATURE - Cpa - para-chloro-phenylalanine
SITE                   10
                       note = MISC_FEATURE - 5FPhe - pentafluoro-phenylalanine
SITE                   15
                       note = MISC_FEATURE - Abu - alpha-aminobutyric acid
SITE                   21
                       note = MISC_FEATURE - Orn - Ornithine
SITE                   27
                       note = MISC_FEATURE - Nle - norleucine
SITE                   28
                       note = MISC_FEATURE - DArg - D-arginine
SITE                   29
                       note = MISC_FEATURE - Har-NH2 - Homoarginine-amide
SEQUENCE: 10
YRDAIFTARF RKVLXQLSAH XLLQDIXRX                                    29

SEQ ID NO: 11          moltype = AA  length = 29
FEATURE                Location/Qualifiers
source                 1..29
                       mol_type = protein
                       organism = synthetic construct
                       note = Synthetic Polypeptide
SITE                   1
                       note = MISC_FEATURE - DPhe-Ada -
                        D-phenylalanine-12-aminododecanoic acid tyrosine
SITE                   2
                       note = MISC_FEATURE - DArg - D-arginine
SITE                   6
                       note = MISC_FEATURE - Cpa - para-chloro-phenylalanine
SITE                   10
                       note = MISC_FEATURE - Tyr(Me) - O-methyl-tyrosine
SITE                   15
                       note = MISC_FEATURE - Abu - alpha-aminobutyric acid
SITE                   21
                       note = MISC_FEATURE - Orn - Ornithine
SITE                   27
                       note = MISC_FEATURE - Nle - norleucine
SITE                   28
                       note = MISC_FEATURE - DArg - D-arginine
SITE                   29
                       note = MISC_FEATURE - Har-NH2 - Homoarginine-amide
SEQUENCE: 11
YRDAIFTARY RKVLXQLSAH XLLQDIXRX                                    29

SEQ ID NO: 12          moltype = AA  length = 29
FEATURE                Location/Qualifiers
source                 1..29
                       mol_type = protein
                       organism = synthetic construct
```

-continued

```
                        note = Synthetic Polypeptide
SITE                    1
                        note = MISC_FEATURE - PhAC-Ada -
                         phenylacetyl-12-aminododecanoic acid tyrosine
SITE                    2
                        note = MISC_FEATURE - DArg - D-arginine
SITE                    6
                        note = MISC_FEATURE - Cpa - para-chloro-phenylalanine
SITE                    10
                        note = MISC_FEATURE - Amp - para-amino-phenylalanine
SITE                    15
                        note = MISC_FEATURE - Abu - alpha-aminobutyric acid
SITE                    21
                        note = MISC_FEATURE - Orn - Ornithine
SITE                    27
                        note = MISC_FEATURE - Nle - norleucine
SITE                    28
                        note = MISC_FEATURE - DArg - D-arginine
SITE                    29
                        note = MISC_FEATURE - Har-NHCH3 - Homoarginine-methylamine
SEQUENCE: 12
YRDAIFTARF RKVLXQLSAH XLLQDIXRX                                    29

SEQ ID NO: 13           moltype = AA  length = 29
FEATURE                 Location/Qualifiers
source                  1..29
                        mol_type = protein
                        organism = synthetic construct
                        note = Synthetic Polypeptide
SITE                    1
                        note = MISC_FEATURE - PhAC-Ada -
                         phenylacetyl-12-aminododecanoic acid tyrosine
SITE                    2
                        note = MISC_FEATURE - DArg - D-arginine
SITE                    6
                        note = MISC_FEATURE - Cpa - para-chloro-phenylalanine
SITE                    10
                        note = MISC_FEATURE - Tyr(Me) - O-methyl-tyrosine
SITE                    15
                        note = MISC_FEATURE - Abu - alpha-aminobutyric acid
SITE                    27
                        note = MISC_FEATURE - Nle - norleucine
SITE                    28
                        note = MISC_FEATURE - DArg - D-arginine
SITE                    29
                        note = MISC_FEATURE - Har-NHCH3 - Homoarginine-methylamine
SEQUENCE: 13
YRDAIFTNRY RKVLXQLSAR KLLQDIXRX                                    29

SEQ ID NO: 14           moltype = AA  length = 29
FEATURE                 Location/Qualifiers
source                  1..29
                        mol_type = protein
                        organism = synthetic construct
                        note = Synthetic Polypeptide
SITE                    1
                        note = MISC_FEATURE - PhAC-Ada -
                         phenylacetyl-12-aminododecanoic acid tyrosine
SITE                    2
                        note = MISC_FEATURE - DArg - D-arginine
SITE                    6
                        note = MISC_FEATURE - Cpa - para-chloro-phenylalanine
SITE                    9
                        note = MISC_FEATURE - Har - Homoarginine
SITE                    10
                        note = MISC_FEATURE - Tyr(Me) - O-methyl-tyrosine
SITE                    15
                        note = MISC_FEATURE - Abu - alpha-aminobutyric acid
SITE                    27
                        note = MISC_FEATURE - Nle - norleucine
SITE                    28
                        note = MISC_FEATURE - DArg - D-arginine
SITE                    29
                        note = MISC_FEATURE - Har-Aoc-NHCH3 -
                         Homoarginine-8-aminooctanoic acid methylamine
SEQUENCE: 14
YRDAIFTNXY RKVLXQLSAR KLLQDIXRX                                    29

SEQ ID NO: 15           moltype = AA  length = 29
```

-continued

```
FEATURE                Location/Qualifiers
source                 1..29
                       mol_type = protein
                       organism = synthetic construct
                       note = Synthetic Polypeptide
SITE                   1
                       note = MISC_FEATURE - 5FPhAC-Ada -
                        pentafluoro-phenylacetyl-12-aminododecanoic acid tyrosine
SITE                   2
                       note = MISC_FEATURE - DArg - D-arginine
SITE                   6
                       note = MISC_FEATURE - Cpa - para-chloro-phenylalanine
SITE                   9
                       note = MISC_FEATURE - Har - Homoarginine
SITE                   10
                       note = MISC_FEATURE - Tyr(Me) - O-methyl-tyrosine
SITE                   15
                       note = MISC_FEATURE - Abu - alpha-aminobutyric acid
SITE                   27
                       note = MISC_FEATURE - Nle - norleucine
SITE                   28
                       note = MISC_FEATURE - DArg - D-arginine
SITE                   29
                       note = MISC_FEATURE - Har-Aoc-NHCH3 -
                        Homoarginine-8-aminooctanoic acid methylamine
SEQUENCE: 15
YRDAIFTNXY RKVLXQLSAR KLLQDIXRX                                    29

SEQ ID NO: 16          moltype = AA  length = 29
FEATURE                Location/Qualifiers
source                 1..29
                       mol_type = protein
                       organism = synthetic construct
                       note = Synthetic Polypeptide
SITE                   1
                       note = MISC_FEATURE - 5FPhAC-Ada -
                        pentafluoro-phenylacetyl-12-aminododecanoic acid tyrosine
SITE                   2
                       note = MISC_FEATURE - DArg - D-arginine
SITE                   6
                       note = MISC_FEATURE - Cpa - para-chloro-phenylalanine
SITE                   9
                       note = MISC_FEATURE - Har - Homoarginine
SITE                   10
                       note = MISC_FEATURE - 5FPhe - pentafluoro-phenylalanine
SITE                   15
                       note = MISC_FEATURE - Abu - alpha-aminobutyric acid
SITE                   21
                       note = MISC_FEATURE - Orn - Ornithine
SITE                   27
                       note = MISC_FEATURE - Nle - norleucine
SITE                   28
                       note = MISC_FEATURE - DArg - D-arginine
SITE                   29
                       note = MISC_FEATURE - Har-NHCH3 - Homoarginine-methylamine
SEQUENCE: 16
YRDAIFTAXF RKVLXQLSAH XLLQDIXRX                                    29

SEQ ID NO: 17          moltype = AA  length = 29
FEATURE                Location/Qualifiers
source                 1..29
                       mol_type = protein
                       organism = synthetic construct
                       note = Synthetic Polypeptide
SITE                   1
                       note = MISC_FEATURE - 5FPhAC-Ada -
                        pentafluoro-phenylacetyl-12-aminododecanoic acid tyrosine
SITE                   2
                       note = MISC_FEATURE - DArg - D-arginine
SITE                   6
                       note = MISC_FEATURE - Cpa - para-chloro-phenylalanine
SITE                   9
                       note = MISC_FEATURE - Har - Homoarginine
SITE                   10
                       note = MISC_FEATURE - 5FPhe - pentafluoro-phenylalanine
SITE                   12
                       note = MISC_FEATURE - Orn - Ornithine
SITE                   15
                       note = MISC_FEATURE - Abu - alpha-aminobutyric acid
```

```
SITE                    21
                        note = MISC_FEATURE - Orn - Ornithine
SITE                    27
                        note = MISC_FEATURE - Nle - norleucine
SITE                    28
                        note = MISC_FEATURE - DArg - D-arginine
SITE                    29
                        note = MISC_FEATURE - Har-Ada-NHCH3 -
                         Homoarginine-12-aminododecanoic acid methylamine
SEQUENCE: 17
YRDAIFTAXF HXVLXQLSAH XLLQDIXRX                                    29

SEQ ID NO: 18           moltype = AA  length = 29
FEATURE                 Location/Qualifiers
source                  1..29
                        mol_type = protein
                        organism = synthetic construct
                        note = Synthetic Polypeptide
SITE                    1
                        note = MISC_FEATURE - 5FPhAC-Ada -
                         pentafluoro-phenylacetyl-12-aminododecanoic acid tyrosine
SITE                    2
                        note = MISC_FEATURE - DArg - D-arginine
SITE                    6
                        note = MISC_FEATURE - Cpa - para-chloro-phenylalanine
SITE                    9
                        note = MISC_FEATURE - Har - Homoarginine
SITE                    10
                        note = MISC_FEATURE - 5FPhe - pentafluoro-phenylalanine
SITE                    12
                        note = MISC_FEATURE - Orn - Ornithine
SITE                    15
                        note = MISC_FEATURE - Abu - alpha-aminobutyric acid
SITE                    21
                        note = MISC_FEATURE - Orn - Ornithine
SITE                    27
                        note = MISC_FEATURE - Nle - norleucine
SITE                    28
                        note = MISC_FEATURE - DArg - D-arginine
SITE                    29
                        note = MISC_FEATURE - Har-Ada-NH2 -
                         Homoarginine-12-aminododecanoic acid amide
SEQUENCE: 18
YRDAIFTAXF HXVLXQLSAH XLLQDIXRX                                    29

SEQ ID NO: 19           moltype = AA  length = 29
FEATURE                 Location/Qualifiers
source                  1..29
                        mol_type = protein
                        organism = synthetic construct
                        note = Synthetic Polypeptide
SITE                    1
                        note = MISC_FEATURE - 5FPhAC-Ada -
                         pentafluoro-phenylacetyl-12-aminododecanoic acid tyrosine
SITE                    2
                        note = MISC_FEATURE - DArg - D-arginine
SITE                    6
                        note = MISC_FEATURE - 5FPhe - pentafluoro-phenylalanine
SITE                    9
                        note = MISC_FEATURE - Har - Homoarginine
SITE                    10
                        note = MISC_FEATURE - Tyr(Me) - O-methyl-tyrosine
SITE                    12
                        note = MISC_FEATURE - Orn - Ornithine
SITE                    15
                        note = MISC_FEATURE - Abu - alpha-aminobutyric acid
SITE                    21
                        note = MISC_FEATURE - Orn - Ornithine
SITE                    27
                        note = MISC_FEATURE - Nle - norleucine
SITE                    28
                        note = MISC_FEATURE - DArg - D-arginine
SITE                    29
                        note = MISC_FEATURE - Har-Ada-NH2 -
                         Homoarginine-12-aminododecanoic acid amide
SEQUENCE: 19
YRDAIFTAXY HXVLXQLSAH XLLQDIXRX                                    29

SEQ ID NO: 20           moltype = AA  length = 29
```

-continued

```
FEATURE                Location/Qualifiers
source                 1..29
                       mol_type = protein
                       organism = synthetic construct
                       note = Synthetic Polypeptide
SITE                   1
                       note = MISC_FEATURE - 5FPhAC-Ada -
                        pentafluoro-phenylacetyl-12-aminododecanoic acid tyrosine
SITE                   2
                       note = MISC_FEATURE - DArg - D-arginine
SITE                   6
                       note = MISC_FEATURE - Cpa - para-chloro-phenylalanine
SITE                   10
                       note = MISC_FEATURE - Tyr(Me) - O-methyl-tyrosine
SITE                   15
                       note = MISC_FEATURE - Abu - alpha-aminobutyric acid
SITE                   21
                       note = MISC_FEATURE - Orn - Ornithine
SITE                   27
                       note = MISC_FEATURE - Nle - norleucine
SITE                   28
                       note = MISC_FEATURE - DArg - D-arginine
SITE                   29
                       note = MISC_FEATURE - Har-Ada-NH2 -
                        Homoarginine-12-aminododecanoic acid amide
SEQUENCE: 20
YRDAIFTNRY RKVLXQLSAH XLLQDIXRX                                    29

SEQ ID NO: 21          moltype = AA  length = 29
FEATURE                Location/Qualifiers
source                 1..29
                       mol_type = protein
                       organism = synthetic construct
                       note = Synthetic Polypeptide
SITE                   29
                       note = MISC_FEATURE - Arg-NH2 - Arginine-amide
SEQUENCE: 21
YADAIFTNSY RKVLGQLSAR KLLQDIMSR                                    29

SEQ ID NO: 22          moltype = AA  length = 29
FEATURE                Location/Qualifiers
source                 1..29
                       mol_type = protein
                       organism = synthetic construct
                       note = Synthetic Polypeptide
SITE                   1
                       note = MISC_FEATURE - PhAC-Ada -
                        phenylacetyl-12-aminododecanoic acid tyrosine
SITE                   2
                       note = MISC_FEATURE - DArg - D-arginine
SITE                   6
                       note = MISC_FEATURE - 5FPhe - pentafluoro-phenylalanine
SITE                   9
                       note = MISC_FEATURE - Har - Homoarginine
SITE                   10
                       note = MISC_FEATURE - Tyr(Me) - O-methyl-tyrosine
SITE                   12
                       note = MISC_FEATURE - Orn - Ornithine
SITE                   15
                       note = MISC_FEATURE - Abu - alpha-aminobutyric acid
SITE                   21
                       note = MISC_FEATURE - Orn - Ornithine
SITE                   27
                       note = MISC_FEATURE - Nle - norleucine
SITE                   28
                       note = MISC_FEATURE - DArg - D-arginine
SITE                   29
                       note = MISC_FEATURE - Har-NH2 - Homoarginine-amide
SEQUENCE: 22
YRDAIFTAXY HXVLXQLSAH XLLQDIXRX                                    29

SEQ ID NO: 23          moltype = AA  length = 29
FEATURE                Location/Qualifiers
source                 1..29
                       mol_type = protein
                       organism = synthetic construct
                       note = Synthetic Polypeptide
SITE                   1
                       note = MISC_FEATURE - PhAC-Ada -
```

```
                       phenylacetyl-12-aminododecanoic acid tyrosine
SITE                   2
                       note = MISC_FEATURE - DArg - D-arginine
SITE                   6
                       note = MISC_FEATURE - Cpa - para-chloro-phenylalanine
SITE                   9
                       note = MISC_FEATURE - Har - Homoarginine
SITE                   10
                       note = MISC_FEATURE - 5FPhe - pentafluoro-phenylalanine
SITE                   12
                       note = MISC_FEATURE - Orn - Ornithine
SITE                   15
                       note = MISC_FEATURE - Abu - alpha-aminobutyric acid
SITE                   21
                       note = MISC_FEATURE - Orn - Ornithine
SITE                   27
                       note = MISC_FEATURE - Nle - norleucine
SITE                   28
                       note = MISC_FEATURE - DArg - D-arginine
SITE                   29
                       note = MISC_FEATURE - Har-NH2 - Homoarginine-amide
SEQUENCE: 23
YRDAIFTAXF HXVLXQLSAH XLLQDIXRX                                    29

SEQ ID NO: 24          moltype = AA  length = 29
FEATURE                Location/Qualifiers
source                 1..29
                       mol_type = protein
                       organism = synthetic construct
                       note = Synthetic Polypeptide
SITE                   1
                       note = MISC_FEATURE - PhAC-Ada -
                        phenylacetyl-12-aminododecanoic acid tyrosine
SITE                   2
                       note = MISC_FEATURE - DArg - D-arginine
SITE                   6
                       note = MISC_FEATURE - Cpa - para-chloro-phenylalanine
SITE                   9
                       note = MISC_FEATURE - Har - Homoarginine
SITE                   10
                       note = MISC_FEATURE - Tyr(Me) - O-methyl-tyrosine
SITE                   15
                       note = MISC_FEATURE - Abu - alpha-aminobutyric acid
SITE                   27
                       note = MISC_FEATURE - Nle - norleucine
SITE                   28
                       note = MISC_FEATURE - DArg - D-arginine
SITE                   29
                       note = MISC_FEATURE - Har-Ada-NH2 -
                        Homoarginine-12-aminododecanoic acid amide
SEQUENCE: 24
YRDAIFTNXY RKVLXQLSAR KLLQDIXRX                                    29

SEQ ID NO: 25          moltype = AA  length = 29
FEATURE                Location/Qualifiers
source                 1..29
                       mol_type = protein
                       organism = synthetic construct
SITE                   1
                       note = pentafluoro-phenylacetyl-12-aminododecanoic acid
                        9-Fluorenylmethoxycarbonyl-O-tert-butyl-L-tyrosine
SITE                   2
                       note =
                        N-(fluorenylmethoxycarbonyl)-Nomega-(2,2,4,6,7-pentamethyl-
                        3H-1-benzofuran-5-yl)sulfonyl-D-arginine
SITE                   3
                       note = 9-fluorenylmethoxycarbonyl-L-aspartic acid
                        4-tert-butyl ester
SITE                   6
                       note = pentafluoro-phenylalanine
SITE                   7
                       note = 9-fluorenylmethoxycarbonyl-O-tert-Butyl-L-threonine
SITE                   9
                       note =
                        N-(fluorenylmethoxycarbonyl)-Nomega-(2,2,4,6,7-pentamethyl-
                        3H-1-benzofuran-5-yl)sulfonyl-L-arginine
SITE                   10
                       note = O-methyl-tyrosine
SITE                   11
```

-continued

```
                     note =
                      N-(fluorenylmethoxycarbonyl)-Nomega-(2,2,4,6,7-pentamethyl-
                      3H-1-benzofuran-5-yl)sulfonyl-L-arginine
SITE                 12
                     note =
                      N-(fluorenylmethoxycarbonyl)-N6-(tert-butoxycarbonyl)-L-lys
                      ine
SITE                 15
                     note = alpha-aminobutyric acid
SITE                 16
                     note = N-(fluorenylmethoxycarbonyl)-N5-trityl-L-glutamine
SITE                 18
                     note = 9-fluorenylmethoxycarbonyl-O-tert-Butyl-L-serine
SITE                 20
                     note =
                      N-(fluorenylmethoxycarbonyl)-Nomega-(2,2,4,6,7-pentamethyl-
                      3H-1-benzofuran-5-yl)sulfonyl-L-arginine
SITE                 21
                     note =
                      N-(fluorenylmethoxycarbonyl)-N6-(tert-butoxycarbonyl)-L-lys
                      ine
SITE                 24
                     note = N-(fluorenylmethoxycarbonyl)-N5-trityl-L-glutamine
SITE                 25
                     note = 9-fluorenylmethoxycarbonyl-L-aspartic acid
                      4-tert-butyl ester
SITE                 27
                     note = norleucine
SITE                 28
                     note =
                      N-(fluorenylmethoxycarbonyl)-Nomega-(2,2,4,6,7-pentamethyl-
                      3H-1-benzofuran-5-yl)sulfonyl-D-arginine
SITE                 29
                     note =
                      N-(fluorenylmethoxycarbonyl)-Nomega-(2,2,4,6,7-pentamethyl-
                      3H-1-benzofuran-5-yl)sulfonyl-L-arginine methylamine-resin
SEQUENCE: 25
YRDAIFTARY RKVLXQLSAR KLLQDIXRR                                    29

SEQ ID NO: 26        moltype = AA  length = 29
FEATURE              Location/Qualifiers
source               1..29
                     mol_type = protein
                     organism = synthetic construct
SITE                 1
                     note = pentafluoro-phenylacetyl-12-aminododecanoic acid
                      tyrosine
SITE                 2
                     note = D-arginine
SITE                 6
                     note = para-chloro-phenylalanine
SITE                 9
                     note = Homoarginine
SITE                 10
                     note = pentafluoro-phenylalanine
SITE                 12
                     note = Ornithine
SITE                 15
                     note = alpha-aminobutyric acid
SITE                 21
                     note = Ornithine
SITE                 27
                     note = norleucine
SITE                 28
                     note = D-arginine
SITE                 29
                     note = Homoarginine-methylamine
SEQUENCE: 26
YRDAIFTAXF HXVLXQLSAH XLLQDIXRX                                    29
```

METHOD OF TREATING AN INFLAMMATORY DISORDER

CROSS REFERENCE TO RELATED APPLICATIONS AND INCORPORATION BY REFERENCE OF MATERIAL

The instant application is a continuation application under 35 U.S.C. 111(a) of international patent application number PCT/US2021/029218 filed on Apr. 26, 2021 designating the United States, which claimed the priority of U.S. provisional patent application 63/015,896, filed on Apr. 27, 2020, which is incorporated by reference in its entirety.

The following patent publications are also hereby incorporated by reference in their entireties and in particular with respect to their disclosures of peptides and methods of producing peptides: U.S. Pat. No. 8,691,942, U.S. 2015/0166617; WO 2005/016953; and WO 2020/163833.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

INCORPORATION OF THE SEQUENCE LISTING

The instant application contains a Sequence Listing which has been submitted electronically in XML file format is hereby incorporated by reference in its entirety. Said XML copy, created on Oct. 27, 2022, is named 7085-0014_SL.xml and is 129,319 bytes in size.

FIELD OF THE INVENTION

The present disclosure is directed to a method of treating an inflammatory disorder, such as sarcoidosis, using a growth hormone-releasing hormone (GHRH) antagonist.

BACKGROUND

Sarcoidosis is a common condition in the US population especially African-Americans with a prevalence of 39 in 100,000 and mostly affects adults aged 20-40 years old[8]. Sarcoidosis related mortality is associated with pulmonary fibrosis[9]. In 2009-2010, there were 1315 sarcoidosis related deaths with an age-adjusted rate of 0.234 per 100,000 year-persons[10]. African Americans have 17 times the mortality rate due to sarcoidosis compared to Caucasian[11]. The etiology of sarcoidosis remains unclear, however it is considered an airborne disease, at least in a subset of patients, since the lungs, eyes and skin are the most affected organs. The possible environmental etiologies include exposure to dusts, microbe-rich environments and chemical agents[12,13]. Various microbial agents have been associated with sarcoidosis. Mycobacteria and *Propionibacterium* are the most cited pathogens in sarcoidosis pathogenesis with the hypothesis that an uncontrolled immune response to particular antigens leads to immunopathology[14-19].

Growth hormone (GH) is central to normal development of the lungs and other organs. GHRH-R agonists mediate GH secretion from pituitary as well as somatic cells.

Antagonists of GHRH-R potently inhibit proliferation of tumor stromal cells.

SUMMARY

Described herein is a method of treating inflammatory disorder, the method comprising administering to a subject in need thereof an effective amount of any one of the GHRH antagonists described herein. In various embodiments, the inflammatory disorder is sarcoidosis (e.g., pulmonary sarcoidosis), pulmonary inflammation or mycobacterial disease. The disclosure further provides use of a GHRH antagonist for treating an inflammatory disorder (e.g., sarcoidosis) or in the preparation of a medicament for treating an inflammatory disorder (e.g., sarcoidosis). The disclosure also provides a GHRH antagonist for use in treating an inflammatory disorder (e.g., sarcoidosis).

In one aspect, the GHRH antagonist comprises the amino acid sequence of Formula I: X0-Tyr-DArg-Asp-Ala-Ile-X6-Thr-X8-X9-X10-X11-X12-Val-Leu-Abu-Gln-Leu-Ser-Ala-X20-X21-Leu-Leu-Gln-Asp-Ile-Nle-DArg-X29-X30 (SEQ ID NO: 1), wherein X0 is 5FPhAC-Ada, p-ClPhAC, D-Phe-Ada, or PhAC-Ada; X6 is 5FPhe or Cpa; X8 is Ala or Asn; X9 is Arg or Har; X10 is Tyr(Me), Amp or 5FPhe; X11 is Arg or His; X12 is Lys or Orn; X20 is Arg or His; X21 is Lys or Orn; X29 is Har, Har-$NH_2$ or Har-$NHCH_3$; and X30 is present or absent and, when present, is Ada-$NH_2$, Ada-NHCH or Ada-$NHCH_2CH_3$, or a pharmaceutically acceptable salt thereof.

In various embodiments, the GHRH antagonist comprises the amino acid sequence of Formula II: 5FPhAC-Ada-Tyr-DArg-Asp-Ala-Ile-X6-Thr-X8-Har-X10-Arg-Lys-Val-Leu-Abu-Gln-Leu-Ser-Ala-Arg-Lys-Leu-Leu-Gln-Asp-Ile-Nle-DArg-X29-X30 (SEQ ID NO: 2), wherein X6 is 5FPhe or Cpa, X8 is Ala or Asn, X10 is Tyr(Me) or 5FPhe, X29 is Har or Har-$NHCH_3$, and X30 is present or absent and, when present, is Ada-$NH_2$ or Ada-$NHCH_3$, or a pharmaceutically acceptable salt thereof.

In various embodiments, the GHRH antagonist comprises the amino acid sequence (a) 5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-$NHCH_3$ (AVR-235, SEQ ID NO: 3); (b) 5FPhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-$NH_2$ (AVR-333, SEQ ID NO: 4); (c) 5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-$NH_2$ (AVR-352, SEQ ID NO: 5); (d) 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-$NH_2$ (AVR-353, SEQ ID NO: 6); or (e) 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-NIe-DArg-Har-Ada-$NHCH_3$ (AVR-354, SEQ ID NO: 7).

In some embodiments, the GHRH antagonist comprises the amino acid sequence 5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-NIe-DArg-NHCH3 (AVR-235, SEQ ID NO: 3). In some embodiments, the GHRH antagonist comprises the amino acid sequence 5FPhAC-Ada-Tyr-DArg-Asp-Ala-Ile-Cpa- Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-NH2 (AVR-333, SEQ ID NO: 4). In some embodiments, the GHRH antagonist comprises the amino acid sequence 5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln- Asp-Ile-Nle-DArg-Har-Ada-NH2 (AVR-352, SEQ ID NO: 5). In some embodiments, the GHRH antagonist comprises the amino acid sequence 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-NH2 (AVR-353, SEQ ID NO: 6). In some embodiments, the GHRH antagonist comprises the amino acid sequence 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-NHCH3 (AVR-354, SEQ ID NO: 7). In some embodiments, the GHRH antagonist comprises the amino acid sequence PhAC-Ada-Tyr-DArg-Asp-Ala-Ile-Cpa-Thr-Ala-Arg-Tyr(Me)-Arg-Lys-Val-Leu-Abu-Gln-Leu-Ser-Ala-His-Orn-Leu-Leu-Gln-Asp-Ile-Nle- DArg-Har-NH2 (AVR-104, SEQ ID NO: 8). In some embodiments, the GHRH antagonist comprises the amino acid sequence PhAC-Ada-Tyr-DArg-Asp-Ala-Ile-Cpa-Thr-Ala-Arg-Tyr-Arg-Lys-Val-Leu-Abu-Gln-Leu-Ser-Ala-Arg-Lys-Leu-Leu-Gln-Asp-Ile-NIe-DArg-Har-NH2 (AVR-107, SEQ ID NO: 9). In some embodiments, the GHRH antagonist comprises the amino acid sequence PhAC-Ada-Tyr-DArg-Asp-Ala-Ile-Cpa-Thr-Ala-Arg-5FPhe-Arg-Lys-Val-Leu-Abu-Gln-Leu-Ser-Ala-His-Orn-Leu-Leu-Gln-Asp-Ile-Nle-DArg-Har-NH2 (AVR-116, SEQ ID NO: 10). In some embodiments, the GHRH antagonist comprises the amino acid sequence D-Phe-Ada-Tyr-DArg-Asp-Ala-Ile-Cpa-Thr-Ala-Arg-Tyr(Me)-Arg-Lys-Val-Leu-Abu-Gln-Leu-Ser-Ala-His-Orn-Leu-Leu-Gln-Asp-Ile-Nle-DArg-Har-NH2 (AVR-120, SEQ ID NO: 11). In some embodiments, the GHRH antagonist comprises the amino acid sequence PhAC-Ada-Tyr-DArg-Asp-Ala-Ile-Cpa-Thr-Ala-Arg-Amp-Arg-Lys-Val-Leu-Abu-Gln-Leu-Ser-Ala-His-Om-Leu-Leu-Gln-Asp-Ile-Nle- DArg-Har-NHCH3 (AVR-201, SEQ ID NO: 12). In some embodiments, the GHRH antagonist comprises the amino acid sequence PhAC-Ada-Tyr-DArg-Asp-Ala-Ile-Cpa-Thr-Asn-Arg-Tyr(Me)-Arg-Lys-Val-Leu-Abu-Gln-Leu-Ser-Ala-Arg-Lys-Leu-Leu-Gln-Asp-Ile-Nle-DArg-Har-NHCH3 (AVR-234, SEQ ID NO: 13). In some embodiments, the GHRH antagonist comprises the amino acid sequence PhAC-Ada-Tyr-DArg-Asp-Ala-Ile-Cpa-Thr-Asn-Har-Tyr (Me)-Arg-Lys-Val-Leu-Abu-Gln-Leu-Ser-Ala-Arg-Lys-Leu-Leu-Gln-Asp-Ile-Nle-DArg-Har-Aoc-NHCH3 (AVR-321, SEQ ID NO: 14). In some embodiments, the GHRH antagonist comprises the amino acid sequence 5FPhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln- Asp-Ile-Nle-DArg-Har-Aoc-NHCH3 (AVR-322, SEQ ID NO: 15). In some embodiments, the GHRH antagonist comprises the amino acid sequence 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-His-Orn-Leu-Leu-Gln-Asp-Ile-Nle-DArg-Har-NHCH3 (AVR-542, SEQ ID NO: 16). In some embodiments, the GHRH antagonist comprises the amino acid sequence 5FPhAC-Ada-Tyr-DArg-Asp-Ala-Ile-Cpa-Thr-Ala-Har-5FPhe-His-Omn-Val-Leu-Abu-Gln-Leu-Ser-Ala-His-Orn-Leu-Leu-Gln-Asp-Ile-Nle-DArg-Har-Ada-NHCH3 (AVR-543, SEQ ID NO: 17). In some embodiments, the GHRH antagonist comprises the amino acid sequence 5FPhAC-Ada-Tyr-DArg-Asp-Ala-Ile-Cpa-Thr-Ala-Har-5FPhe-His-Orn-Val-Leu-Abu-Gln-Leu-Ser-Ala-His-Orn-Leu-Leu-Gln-Asp-Ile-Nle-DArg-Har-Ada-NH2 (AVR-552, SEQ ID NO: 18). In some embodiments, the GHRH antagonist comprises the amino acid sequence 5FPhAC-Ada-Tyr-DArg-Asp-Ala-Ile-5FPhe-Thr-Ala-Har-Tyr(Me)-His-Orn-Val-Leu-Abu-Gln-Leu-Ser-Ala-His-Orn-Leu-Leu-Gln-Asp-Ile-Nle-DArg-Har-Ada-NH2 (AVR-553, SEQ ID NO: 19). In some embodiments, the GHRH antagonist comprises the amino acid sequence 5FPhAC-Ada-Tyr-DArg-Asp-Ala-Ile-Cpa-Thr-Asn-Arg-Tyr(Me)-Arg-Lys-Val-Leu-Abu-Gln-Leu-Ser-Ala-His-Orn-Leu-Leu-Gln-Asp-Ile- Nle-DArg-Har-Ada-NH2 (AVR-620, SEQ ID NO: 20), or those amino acid sequences listed in FIG. 8.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. The terms “comprising,” “having,” “including,” and “containing” are to be construed as open-ended terms unless otherwise noted. If aspects of the invention are described as “comprising” a feature, embodiments also are contemplated “consisting of” or “consisting essentially of” the feature. The use of any and all examples, or exemplary language (e.g., “such as”) provided herein, is intended merely to better illustrate the disclosure and does not pose a limitation on the scope of the disclosure unless otherwise claimed. No language in the specification should be construed as indicating any non-claimed element as essential to the practice of the disclosure. Other than in the operating examples, or where otherwise indicated, all numbers expressing quantities of ingredients or reaction conditions used herein should be understood as modified in all instances by the term “about” as that term would be interpreted by the person skilled in the relevant art.

Although the applicant(s) invented the full scope of the invention described herein, the applicants do not intend to claim subject matter described in the prior art work of others. Therefore, in the event that statutory prior art within the scope of a claim is brought to the attention of the applicant(s) by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE FIGURES

FIG. 7 is a table listing the amino acid replacements in AVR-GHRH antagonists compared to MIA-602 and MIA-690 peptides.

FIG. 8 is a table listing the structures of various AVR antagonists.

DETAILED DESCRIPTION

Figure 1:
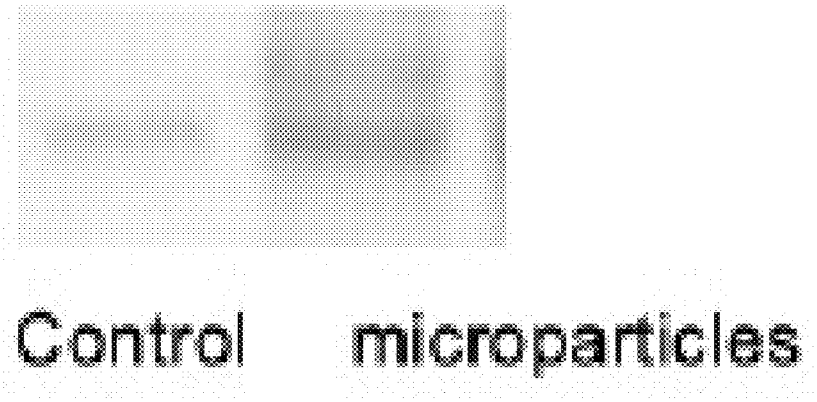
FIG. 1 shows a representative Western blot image of GHRHR expression in an ex vivo granuloma model developed from PBMC of a sarcoidosis patient.

The disclosure provides a method of treating an inflammatory disorder, such as sarcoidosis (e.g., pulmonary sarcoidosis). The method comprises administering a GHRH antagonist to mammalian subject in need thereof. The data set forth herein reveals that GHRH antagonists significantly reduce inflammation in an in vivo model of sarcoidosis.

Growth hormone-releasing hormone (GHRH) is secreted by the hypothalamus and acts on the pituitary gland to stimulate the release of growth hormone (GH). The pituitary GHRH receptor (pGHRH-R) is a seven-transmembrane-domain receptor coupled to G-protein. Rekasi et al., PNAS 97 (19), 10561-6 (2000); Havt et al., PNAS 102 (48), 17424-9 (2005). The pGHRH-R, as well as its truncated splice variants (SV) is expressed in various human tissues. SV1 differs from pGHRH-R in the amino-terminal extracellular domain. Rekasi, supra. The GHRH fragment comprising residues 1 to 29, or GHRH(1-29), demonstrates biological activity on the pituitary. This fragment retains 50% or more of the potency of native GHRH. Many synthetic analogs of GHRH, based on the structure of hGH-RH(1-29)$NH_2$ peptide have been prepared are contemplated herein for use in the context of the method. hGHRH (1-29)$NH_2$ has the following amino acid sequence: Tyr-Ala-Asp-Ala-Ile$^5$-Phe-Thr-Asn-Ser-Tyr$^{10}$-Arg-Lys-Val-Leu-Gly$^{15}$-Gln-Leu-Ser-Ala-Arg$^{20}$-Lys-Leu-Leu-Gln-Asp$^{25}$-Ile-Met-Ser-Arg$^{29}$-$NH_2$(SEQ ID NO: 21).

In one aspect, described herein is a method of treating an inflammatory disorder, the method comprising administering to a subject in need thereof an effective amount of a GHRH antagonist comprising the amino acid sequence of Formula I: X0-Tyr-DArg-Asp-Ala-Ile-X6-Thr-X8-X9-X10-X11-X12-Val-Leu-Abu-Gln-Leu-Ser-Ala-X20-X21-Leu-Leu-Gln-Asp-Ile-Nle-DArg-X29-X30 (SEQ ID NO: 1), wherein X0 is 5FPhAC-Ada, p-ClPhAC, D-Phe-Ada, or PhAC-Ada; X6 is 5FPhe or Cpa; X8 is Ala or Asn; X9 is Arg or Har; X10 is Tyr(Me), Amp or 5FPhe; X11 is Arg or His; X12 is Lys or Orn; X20 is Arg or His; X21 is Lys or Orn; X29 is Har, Har-$NH_2$ or Har-$NHCH_3$; and X30 is present or absent and, when present, is Ada-$NH_2$, Ada-NHCH or Ada-$NHCH_2CH_3$, or a pharmaceutically acceptable salt thereof.

In various embodiments, the GHRH antagonist comprises the amino acid sequence of Formula II: 5FPhAC-Ada-Tyr-DArg-Asp-Ala-Ile-X6-Thr-X8-Har-X10-Arg-Lys-Val-Leu-Abu-Gln-Leu-Ser-Ala-Arg-Lys-Leu-Leu-Gln-Asp-Ile-Nle-DArg-X29-X30 (SEQ ID NO: 2), wherein X6 is 5FPhe or Cpa, X8 is Ala or Asn, X10 is Tyr(Me) or 5FPhe, X29 is Har or Har-$NHCH_3$, and X30 is present or absent and, when present, is Ada-$NH_2$ or Ada-$NHCH_3$, or a pharmaceutically acceptable salt thereof.

In some embodiments, the GHRH antagonist comprises the amino acid sequence 5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-NHCH3 (AVR-235, SEQ ID NO: 3). In some embodiments, the GHRH antagonist comprises the amino acid sequence 5FPhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-NH2 (AVR-333, SEQ ID NO: 4). In some embodiments, the GHRH antagonist comprises the amino acid sequence 5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-NH2 (AVR-352, SEQ ID NO: 5). In some embodiments, the GHRH antagonist comprises the amino acid sequence 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-NH2 (AVR-353, SEQ ID NO: 6). In some embodiments, the GHRH antagonist comprises the amino acid sequence 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-NHCH3 (AVR-354, SEQ ID NO: 7). In some embodiments, the GHRH antagonist comprises the amino acid sequence PhAC-Ada-Tyr-DArg-Asp-Ala-Ile-Cpa-Thr-Ala-Arg-Tyr(Me)-Arg-Lys-Val-Leu-Abu-Gln-Leu-Ser-Ala-His-Orn-Leu-Leu-Gln-Asp-Ile-Nle- DArg-Har-NH2 (AVR-104, SEQ ID NO: 8). In some embodiments, the GHRH antagonist comprises the amino acid sequence PhAC-Ada-Tyr-DArg-Asp-Ala-Ile-Cpa-Thr-Ala-Arg-Tyr-Arg-Lys-Val-Leu-Abu-Gln-Leu-Ser-Ala-Arg-Lys-Leu-Leu-Gln-Asp-Ile-Nle-DArg-Har-NH2 (AVR-107, SEQ ID NO: 9). In some embodiments, the GHRH antagonist comprises the amino acid sequence PhAC-Ada-Tyr-DArg-Asp-Ala-Ile-Cpa-Thr-Ala-Arg-5FPhe-Arg-Lys-Val-Leu-Abu-Gln-Leu-Ser-Ala-His-Orn-Leu-Leu-Gln-Asp-Ile-Nle-DArg-Har-NH2 (AVR-116, SEQ ID NO: 10). In some embodiments, the GHRH antagonist comprises the amino acid sequence D-Phe-Ada-Tyr-DArg-Asp-Ala-Ile-Cpa-Thr-Ala-Arg-Tyr(Me)-Arg-Lys-Val-Leu-Abu-Gln-Leu-Ser-Ala-His-Orn-Leu-Leu-Gln-Asp-Ile-Nle-DArg-Har-NH2 (AVR-120, SEQ ID NO: 11). In some embodiments, the GHRH antagonist comprises the amino acid sequence PhAC-Ada-Tyr-DArg-Asp-Ala-Ile-Cpa-Thr-Ala-Arg-Amp-Arg-Lys-Val-Leu-Abu-Gln-Leu-Ser-Ala-His-Orn-Leu-Leu-Gln-Asp-Ile-Nle- DArg-Har-NHCH3 (AVR-201, SEQ ID NO: 12). In some embodiments, the GHRH antagonist comprises the amino acid sequence PhAC-Ada-Tyr-DArg-Asp-Ala-Ile-Cpa-Thr-Asn-Arg-Tyr(Me)-Arg-Lys-Val-Leu-Abu-Gln-Leu-Ser-Ala-Arg-Lys-Leu-Leu-Gln-Asp-Ile-Nle-DArg-Har-NHCH3

(AVR-234, SEQ ID NO: 13). In some embodiments, the GHRH antagonist comprises the amino acid sequence PhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Aoc-NHCH3 (AVR-321, SEQ ID NO: 14). In some embodiments, the GHRH antagonist comprises the amino acid sequence 5FPhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln- Asp-Ile-Nle-DArg-Har-Aoc-NHCH3 (AVR-322, SEQ ID NO: 15). In some embodiments, the GHRH antagonist comprises the amino acid sequence 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-His-Orn-Leu-Leu-Gln-Asp-Ile-Nle-DArg-Har-NHCH3 (AVR-542, SEQ ID NO: 16). In some embodiments, the GHRH antagonist comprises the amino acid sequence 5FPhAC-Ada-Tyr-DArg-Asp-Ala-Ile-Cpa-Thr-Ala-Har-5FPhe-His-Om-Val-Leu-Abu-Gln-Leu-Ser-Ala-His-Orn-Leu-Leu-Gln-Asp-Ile-Nle-DArg-Har-Ada-NHCH3 (AVR-543, SEQ ID NO: 17). In some embodiments, the GHRH antagonist comprises the amino acid sequence 5FPhAC-Ada-Tyr-DArg-Asp-Ala-Ile-Cpa-Thr-Ala-Har-5FPhe-His-Orn-Val-Leu-Abu-Gln-Leu-Ser-Ala-His-Orn-Leu-Leu-Gln-Asp-Ile-Nle-DArg-Har-Ada-NH2 (AVR-552, SEQ ID NO: 18. In some embodiments, the GHRH antagonist comprises the amino acid sequence 5FPhAC-Ada-Tyr-DArg-Asp-Ala-Ile-5FPhe-Thr-Ala-Har-Tyr(Me)-His-Orn-Val-Leu-Abu-Gln-Leu-Ser-Ala-His-Orn-Leu-Leu-Gln-Asp-Ile-Nle-DArg-Har-Ada-NH2 (AVR-553, SEQ ID NO: 19). In some embodiments, the GHRH antagonist comprises the amino acid sequence 5FPhAC-Ada-Tyr-DArg-Asp-Ala-Ile-Cpa-Thr-Asn-Arg-Tyr(Me)-Arg-Lys-Val-Leu-Abu-Gln-Leu-Ser-Ala-His-Orn-Leu-Leu-Gln-Asp-Ile- Nle-DArg-Har-Ada-NH2 (AVR-620, SEQ ID NO: 20).

In various embodiments, the GHRH antagonist comprises the amino acid sequence (a) 5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-$NHCH_3$ (AVR-235, SEQ ID NO: 3); (b) 5FPhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-$NH_2$ (AVR-333, SEQ ID NO: 4); (c) 5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-$NH_2$ (AVR-352, SEQ ID NO: 5); (d) 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-$NH_2$ (AVR-353, SEQ ID NO: 6); or (e) 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-$NHCH_3$ (AVR-354, SEQ ID NO: 7).

Full names of abbreviations of various non-natural amino acids are provided: PhAc (phenylacetyl), Ac-Ada (acetyl-12-aminododecanoyl), PhAc-Ada (phenylacetyl 12-aminododecanoyl), Cpa (para-chlorophenylalanine), Har (homoarginine), Abu (alpha-aminobutyric acid), and Orn (ornithine).

In various embodiments, administration of the GHRH antagonist peptide reduces CD209f expression by at least 1%, 3%, 5%, 10%, 20%, 30%, 50%, 100% or more. In various embodiments, administration of the GHRH antagonist peptide reduces iNOS expression by at least 1%, 3%, 5%, 10%, 20%, 30%, 50%, 100% or more.

The disclosure provides a method of treating an inflammatory disorder. In various aspects, the inflammatory disorder is sarcoidosis (e.g., pulmonary sarcoidosis), pulmonary inflammation, chronic obstructive pulmonary disease (COPD), asthma, severe pneumonia, interstitial lung disease, pulmonary vasculitis, inflammatory occupational lung, or mycobacterial disease. In a preferred embodiment, the disclosure provides a method of treating sarcoidosis (such as pulmonary sarcoidosis) in a subject in need thereof. "Treating" sarcoidosis (or any other inflammatory disorder) does not require a 100% remission. Any decrease in sarcoidosis or symptoms of sarcoidosis (e.g., inflammation, granuloma formation, or granuloma size), or increase in quality of life, constitutes a beneficial biological effect in a subject. The progress of the method of treating sarcoidosis (or other inflammatory disorder) can be ascertained using any suitable method, such as biomarker detection/measurement in a biological (e.g., blood) sample, chest imaging (e.g., CT-scan), and PET-CT scan. In certain aspects, the method provides a reduction or improvement in a disease indicator, parameter, or symptom, such as a reduction in angiotensin converting enzyme (ACE), SIL2R, or CRP biomarkers, by at least 50%, at least 65%, at least 75%, at least 80%, at least 85%, at least 90%, at least 95% or by at least 99% as compared to pre-treatment, or a reduction in a disease indicator, parameter, or symptom by at least 50% compared to that achieved by treatment with prednisone (administered prior to the instant method or in a matched patient). In various aspects, "treatment" also includes stabilization of the disorder, i.e., controlled or no further progression of the disorder (e.g., granuloma burden does not increase, or increases by less than 10%, preferably less than 5%, within a given timeframe). In various aspects, administration of the GHRH antagonist delays onset or prevents the onset of an inflammatory disease, such as sarcoidosis.

Alternatively or in addition, treatment as described herein optionally improves the stage of the disorder or reduces the severity within a stage. Commonly used stages for sarcoidosis includes: stage I, granulomas located mainly in lymph nodes; stage II, granulomas located in lungs and lymph nodes; stage III, granulomas located mainly in lungs with shrinking lymph nodes; stage IV, pulmonary fibrosis.

Sarcoidosis disease progression is determined using any of a variety of clinical techniques, such as biopsy of the affected organ(s) to identify granulomas, blood test, bronchoscopy, X-ray, neurological tests (e.g., electromyography, evoked potentials, spinal taps, or nerve conduction tests), high-resolution computed tomography (CT) scans, magnetic resonance imaging (MRI), positron electron tomography (PET) scans, pulmonary function tests, and ultrasound.

A particular administration regimen for a particular subject will depend, in part, upon the amount of antagonist administered, the route of administration, and the cause and extent of any side effects. The amount administered to the subject (e.g., human) in accordance with the disclosure should be sufficient to affect the desired response (i.e., ameliorate, prevent or improve an unwanted condition, disease or symptom of a patient) over a reasonable time frame. An effective amount of the GHRH antagonist is typically an amount such that when it is administered in a physiologically tolerable excipient composition, it is sufficient to achieve an effective systemic concentration or local concentration in target tissue to achieve the desired biological effect.

The doses of GHRH antagonist compositions administered to a subject can be chosen in accordance with different parameters, such as the mode of administration used. In the event that a response in a subject is insufficient at the initial doses applied, higher doses (or effectively higher doses by a different, more localized delivery route) may be employed to the extent that patient tolerance permits.

In general, doses of GHRH antagonist are formulated and administered in doses between 0.5 mg/kg to about 500 mg/kg. In some embodiments, the GHRH antagonist is formulated and administered at a dose ranging from 0.5 mg/kg to about 5 mg/kg, 0.5 mg/kg to about 200 mg/kg, or about 1 mg/kg to about 100 mg/kg, or about 1 mg/kg to about 50 mg/kg. In some embodiments, doses of GHRH antagonist are formulated and administered in a dose of ranging from about 30 mg to about 300 mg (or about 30 mg to about 50 mg, or about 30 mg to about 100 mg, or about 50 mg to about 150 mg, or about 75 mg to about 200 mg, or about 100 mg to about 300 mg).

The GHRH antagonist may be administered daily, at least once a week, at least twice a week, at least three times a week, at least four times a week, at least five times a week, six times a week, every two weeks, every three weeks, every four weeks, every five weeks or every six weeks. The treatment period (entailing multiple administrations of the antagonist) will depend on the nature and severity of the disease, as well as the existence of any side effects. Examples of treatment periods include, but are not limited to, 2 weeks, 3 weeks, 1 month, 2 months, 3 months, 4 months, 5 months, 6 months, 9 months, and 12 months.

Methods of administration may include, but are not limited to, oral administration and parenteral administration, including but not limited to, intradermal, intramuscular, intraperitoneal, intravenous, intraarterial, subcutaneous, epidural, sublingual, intranasal, intracerebral, intraventricular, intrathecal, intravaginal, transdermal, rectally, inhalation, intrapulmonary, intra-airway, intrabronchial, intratracheal, or topical (e.g., to the ears, nose, eyes, or skin) delivery. The antagonist is administered subcutaneously in various aspects. In other aspects, such as aspects wherein the subject suffers from pulmonary sarcoidosis, the antagonist is administered via intranasal, inhalation, intrapulmonary, intra-airway, intrabronchial, or intratracheal delivery.

Optionally, the GHRH antagonist is administered either alone or in combination (concurrently or serially) with other pharmaceuticals, optionally as a single, combined formulation or as separate compositions. In some aspects, the method comprises administering multiple GHRH antagonists. Alternatively or in addition, the GHRH antagonist is optionally administered in combination with other anti-inflammatories, such as a steroid. Alternatively or in addition, the GHRH antagonist is optionally administered in combination with one or more disease-modifying antirheumatic drugs (DMARDs; e.g., methotrexate, azathioprine, or leflunomide), a monoclonal antibody (e.g., infliximab, adalimumab, rituximab, or golimumab), colchicine, hormone therapy (e.g., corticotropin), an antibiotic, and/or pentoxifylline.

Additional therapeutic agents or therapies contemplated for use with the GHRH antagonist described herein include, but are not limited to, corticosteroids, methotrexate (e.g. Trexall) and azathioprine (e.g. Azasan, Imuran), hydroxychloroquine, TNF-alpha inhibitors (e.g. Infliximab, Adalimumab), surgery, physical therapy and other agents.

Compositions comprising a GHRH antagonist described herein are also provided. The compositions comprise, for example, a GHRH antagonist and, optionally, pharmaceutically acceptable carrier. As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term denotes an organic or inorganic ingredient, natural or synthetic, with which the active ingredient is combined to facilitate the application. The components of the pharmaceutical compositions also are capable of being co-mingled with the GHRH antagonist, and with each other, in a manner such that there is no interaction which would substantially impair the desired pharmaceutical efficacy. The pharmaceutical compositions may contain suitable buffering agents, including, e.g., acetic acid in a salt; citric acid in a salt; boric acid in a salt; and phosphoric acid in a salt. The pharmaceutical compositions used in the foregoing methods preferably are sterile and contain a GHRH antagonist for producing the desired response in a unit of weight or volume suitable for administration to a patient.

The disclosure further provides use of a GHRH antagonists described herein or a pharmaceutically acceptable salt thereof for treating an inflammatory disorder (e.g., sarcoidosis) or in the preparation of a medicament for treating an inflammatory disorder (e.g., sarcoidosis). The disclosure also provides a GHRH antagonist or a pharmaceutically acceptable salt thereof for use in treating an inflammatory disorder (e.g., sarcoidosis).

The term "subject" includes, but is not limited to, human and non-human mammals such as wild, domestic and farm animals. Preferably, the subject is a human. The subject may be suffering from any form of inflammatory disorder, such as sarcoidosis (i.e., sarcoidosis in any organ, such as the lungs). Administration of GHRH antagonist compositions to mammals other than humans, e.g., for testing purposes or veterinary therapeutic purposes, is carried out under substantially the same conditions as described above.

All publications and patents mentioned herein are hereby incorporated by reference in their entirety as if each individual publication or patent was specifically and individually indicated to be incorporated by reference. In case of conflict, the present application, including any definitions herein, will control.

The invention may be more readily understood by reference to the following example, which are given to illustrate the invention and not in any way to limit its scope.

EXAMPLES

Example 1—Upregulation of GHRHR in an Ex Vivo Sarcoidosis Model

The presence of GHRHR in immune cells was investigated. Western blots were performed on protein extracted from patients with sarcoidosis, challenged or unchallenged with *Mycobacterium abscessus* (MAB) cell wall microparticles. As shown in FIG. 1, after challenging with microparticles, the expression of GHRHR protein was increased (i.e., up regulated).

Example 2—Upregulation of GHRHR in an In Vivo Sarcoidosis Model

A mouse model of pulmonary sarcoidosis was previously established in C57B1/6 mice. Microparticles (*Mycobacterium abscessus*) developed in-house were administered intratracheally. The tongue was pulled out with a small spatula and microparticle was inserted into the trachea using a 20 G angio-catheter tube and advanced to main bronchus until reach to resistant. After tube placement, microparticles were administered (first dose of 50 μL=$5\times10^8$, followed by up to 3 doses of 20 μL=$2\times10^8$ of CFU of *M. abscessus*). The control group received only 20 μL PBS intratracheally.

To demonstrating accuracy of pulmonary installation, lung tissue was stained with methylene blue before killing the mouse. The lung tissue was fixed in formalin and cut for histology. Developed noncaseating granuloma in the mouse lung was visualized with H&E staining and immunohistochemistry staining for CD68 macrophage marker, CD4 marker, and PD-L1.

To test if GHRHR protein is overexpressed in this granulomatous reaction, immunofluorescence staining was used to show the receptor expression in the lungs of control and challenged mice. The expression of GHRHR was significantly increased after challenging with MAB microparticles.

Example 3—AVR Treated Mice Show Lower Lung Inflammation Score

Three groups of mice demonstrating pulmonary sarcoidosis were established alongside a fourth non-treated group which served as a control exhibiting no sarcoidosis. One sarcoidosis group received AVR ("AVR group"), administered via subcutaneous injection, 5 microgram per mouse daily. Another sarcoidosis group received steroid treatment (methyl-prednisone, the current first line treatment for sarcoidosis) ("solu-medrol group"), and the final group received only saline ("granuloma group"). After 3 weeks mice were sacrificed and graded the inflammation in the lung samples.

Two mg of AVR-352 was added to 0.5 ml DMSO. After dissolving, 1,2-propanediol 10% was added to reach a volume of 40 ml. The fluid was sterilized by passing through a 0.22-micron filter. Aliquots were stored at −80° C. before injection to mice.

Figure 2:
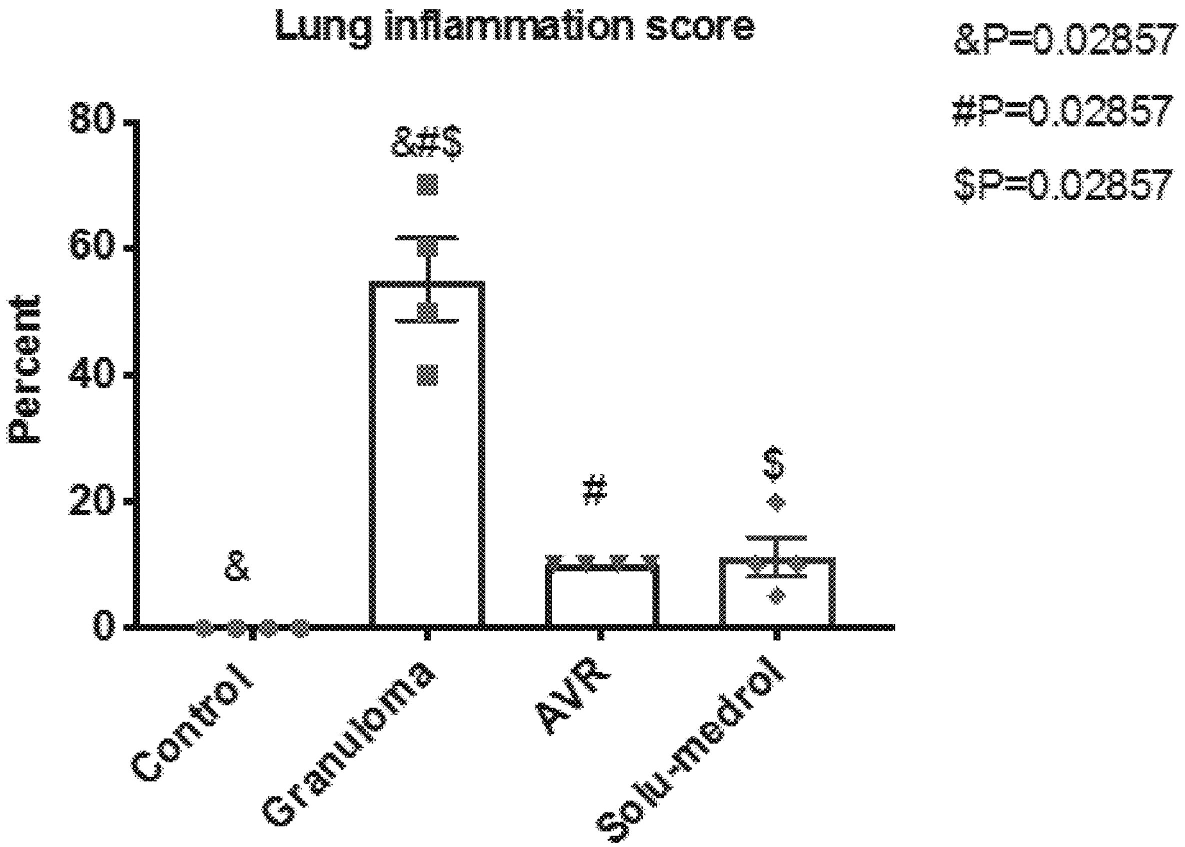
FIG. 2 is a graph showing the percentage of lung inflammation in a control, granuloma treated with saline (Granuloma), granuloma treated with a-MSH, granuloma treated with AVR, and granuloma treated with Solu-Medrol (methyl prednisolone).

As shown in FIG. 2, the granuloma group had significant inflammation in the lung. The mice treated with AVR had significantly lower inflammation scores. Steroid (Solu-Medrol) treatment showed less effect than AVR. The results described demonstrate a representative growth hormone releasing hormone receptor antagonist is effective in treating sarcoidosis, and reduced inflammation to a greater extent that the first line treatment for sarcoidosis in a clinically relevant animal model.

Example 4—AVR Treatment Reduced INOS Expression in the Challenged Lung Mice

Figure 3:
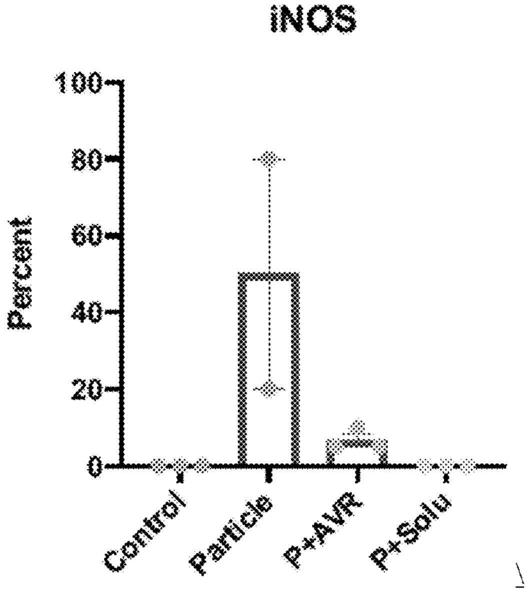
FIG. 3 is a graph showing the percentage of iNOS expression in the challenged lung mice in the MAB microparticle challenged, microparticles and AVR (P+AVR), and steroid treated groups (P+Solu).
Figure 4A:
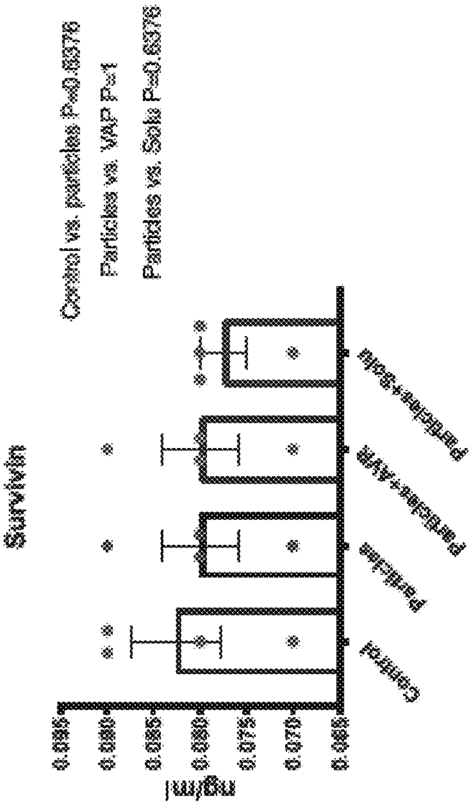
FIGS. 4A-4D are graphs showing changes in apoptosis-related proteins in the MAB microparticle challenged, AVR (Particles+AVR), and steroid treated groups (Particles+Solu).
Figure 4B:
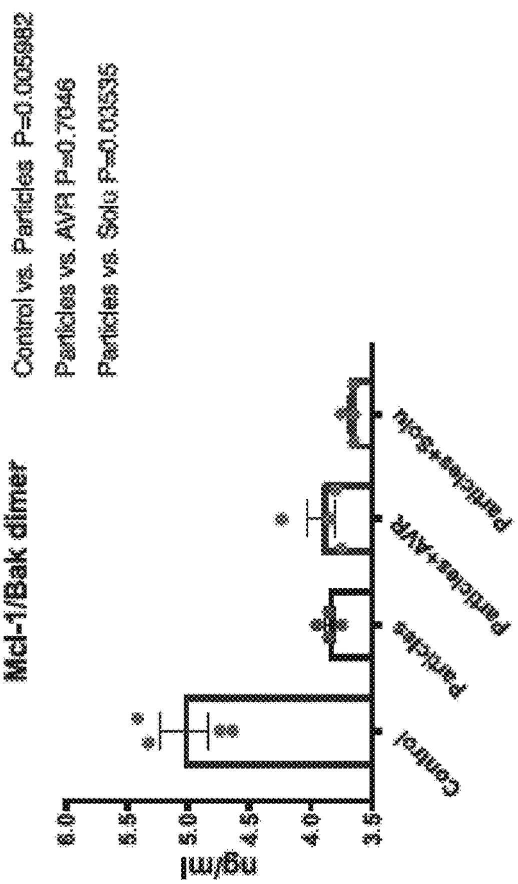
Figure 4C:
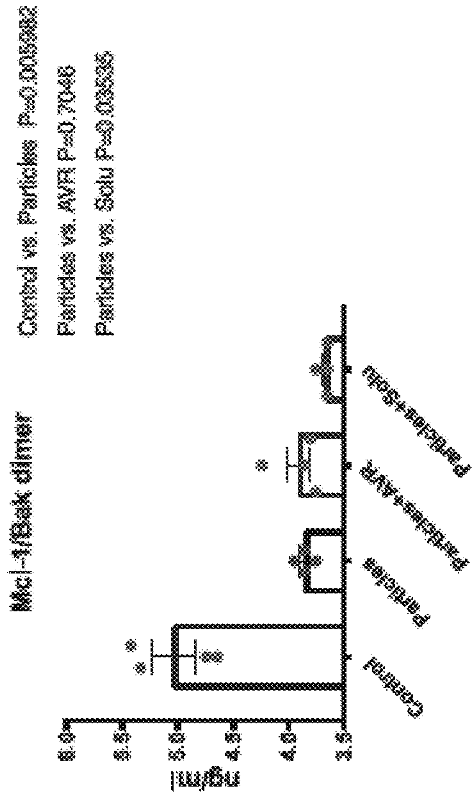
Figure 4D:
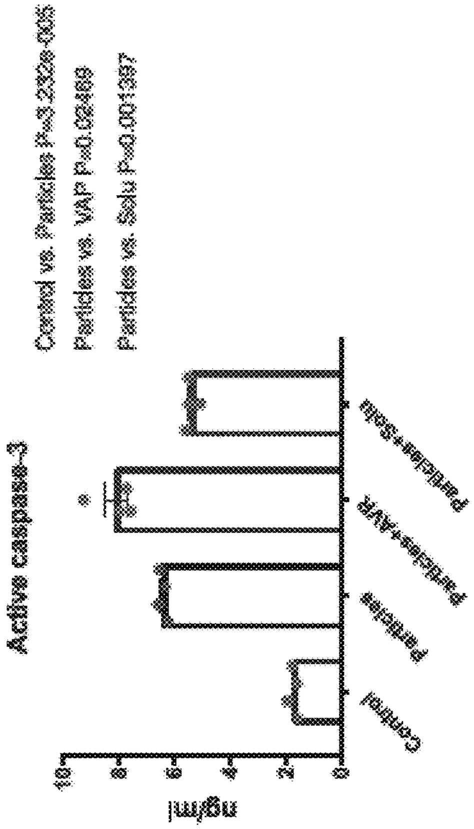
Figure 5A:
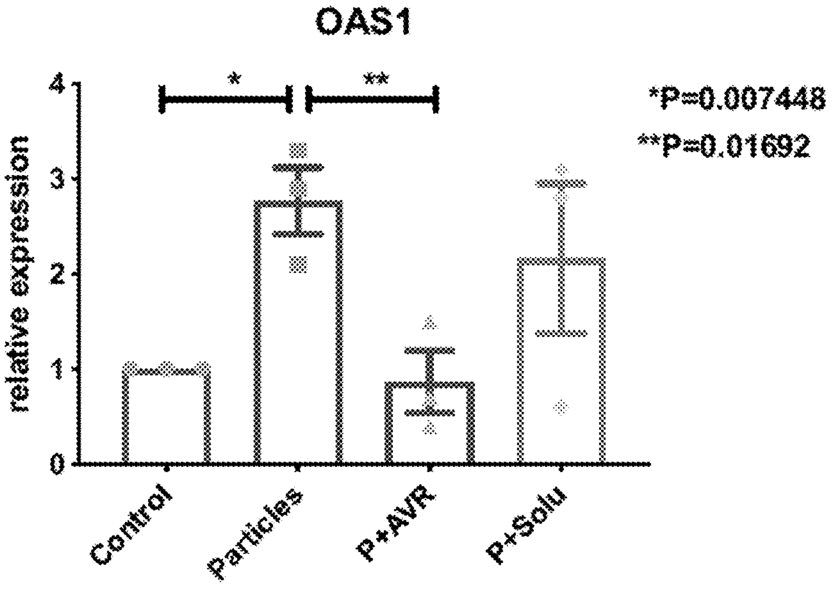
FIGS. 5A-5D show Western blot results for IL2, ISG15, OAS1 from mice lung, control, challenged, challenged with AVR treatment (P+AVR), solu-medrol (steroid) (P+Solu) treatment.
Figure 5B:
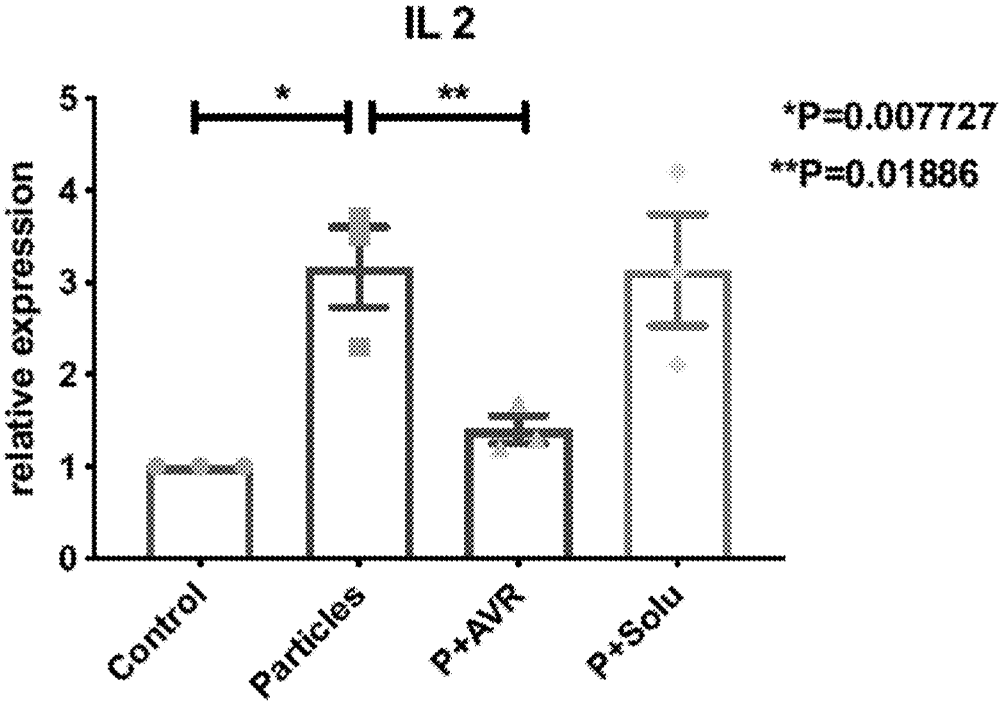
Figure 5C:
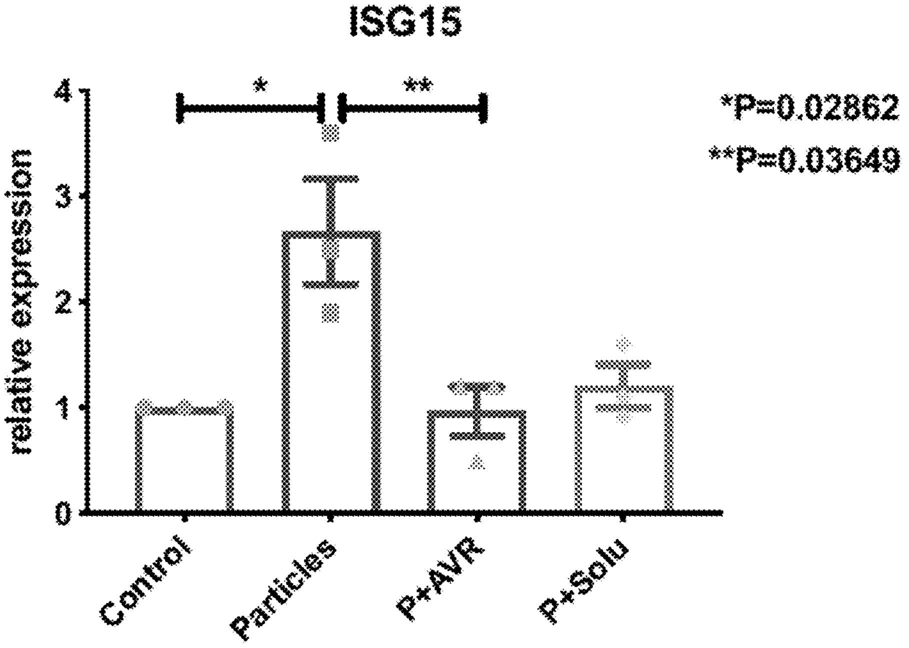
Figure 5D:
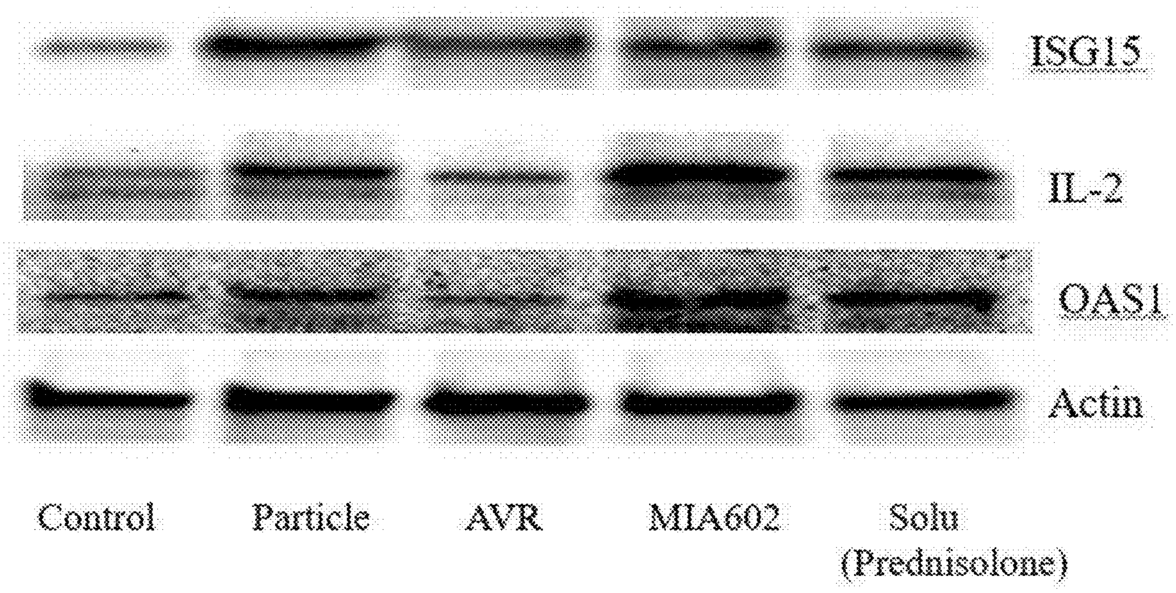

Inducible Nitric oxide synthase (iNOS) plays important role in immune response to microbes. NO can control the production of Th1 immune responses by modulating IL-12 expression. NO plays an important inhibitory role in Th17 differentiation. Th17 cells play a key role in inflammatory diseases. NO directly affects the activity of many proteins via tyrosine nitration. To test whether AVR reduces iNOS expression in an inflammation model, lungs from mouse models described in Example 3 were evaluated for iNOS. As shown in FIG. 3, while MAB microparticle treatment alone ("particle") significantly increased iNOS expression relative to the control, MAB microparticle treatment combined with AVR ("P+AVR") significantly reduced MAB-induced increased iNOS expression similar to reduced MAB-induced increased iNOS expression MAB microparticle treatment combined with Solu-Medrol steroid treatment ("P+Solu").

Example 5—AVR Treatment Induced Apoptosis in Human PBMC

GHRHR antagonists induce apoptosis in cancer cells. The effects of GHRHR antagonist in immune cells still remains unclear. The ability of AVR to induce apoptosis in an ex vivo sarcoidosis model using PBMC of five subjects with confirmed pulmonary sarcoidosis was characterized.

PBMC samples were grouped as "control" (not challenged), "particles" (granuloma), "particles+AVR" (granuloma treated with 1 microM AVR), and "particles+Solu" (granuloma treated with methyl prednisolone as positive control). The "particle" groups were challenged with equal to 10:1 treatment with MAB microparticles. Media from all groups were removed 48 h after of treatments. Survivn, MCL-1/Bak Dimer, BClxL/Bak dimer, and active caspase 3 concentrations were measured using multiplex Elisa instrument and compared using t-test.

As shown in FIG. 4A-4D, the concentration of MC1-1/Bak dimer was significantly reduced after MAB microparticle challenge and treatment with steroid. Active capase-3 concentration significantly increased after challenging cells with MAB microparticles and treatment with AVR and steroid. Increasing active caspase 3 may suggest apoptosis induction.

Example 6—AVR Treatment Reduced Cytokine Expression in the Challenged Lung Mice The effects of AVR on IL2 (T helper 1 cytokine) and Type I interferon cytokines (OAS1 and ISG15) were measured and compared in the lungs of mice models prepared as set forth in Example 3. Expression of all three cytokines increased in response to MAB microparticle challenge, and was reduced significantly in subjects treated with AVR, as shown in FIG. 5A-5D.

Example 7—AVR Treatment Reduced CD209f Expression in the Challenged Lung Mice Whole gene expression was analyzed using RNASeq. Harvested lung from control, challenged, and treatment groups generated as described in Example 3 were used. RNA was isolated and RNASeq was performed at Genomic center at University of Miami. Among 55343 coding and noncoding genes, 26 genes were expressed significantly differently between challenged groups and challenged grous treated with AVR (FC 2.5 with FDR<0.05). A heatmap was generated for the differentiating genes between challenged mice with MAB microparticles versus challenged mice with AVR treatment.

Figure 6:
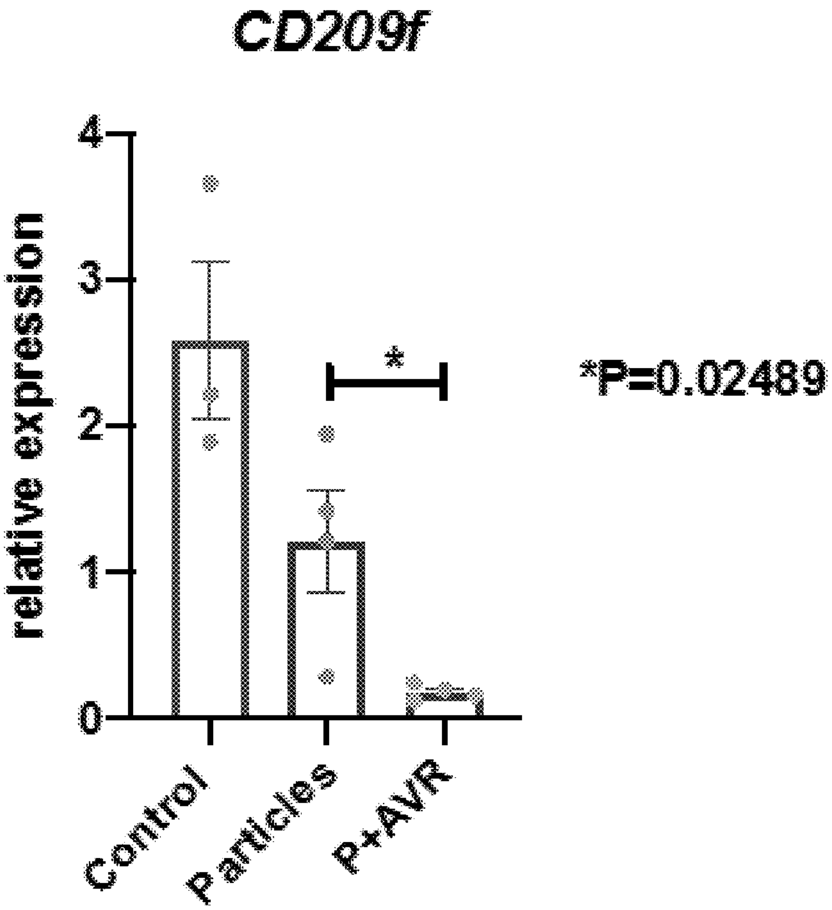
FIG. 6 shows CD209f gene expression changes after microparticles (particles) and microparticles and AVR treatment (P+AVR).

The CD209f gene encodes a receptor in dendritic cells and is significantly downregulated by AVR, as shown in FIG. 6. This suggests that downregulation of CD209f prevents dendritic cell activation and, consequently, reduces T cell activity.

In summary, disclosed herein are the therapeutic effects of AVR in a model of lung sarcoidosis granuloma. These results support for the first time that new class of Growth Hormone Releasing Hormone Receptor Antagonist (AVR) is a new therapeutic agent for inflammatory diseases, such as sarcoidosis.

Example 8—Synthesis of GHRH Antagonists

A plurality of AVR growth hormone-releasing hormone (GHRH) antagonists were synthesized using Fmoc-chemistry. The resulting GHRH antagonists contained modifications at positions 0, 6, 8, 10, 11, 12, 20, 21, 29 and 30 compared to a reference set of GHRH antagonists ("MIA" peptides). See FIGS. 7 and 8.

C-terminal methylamide or ethylamide AVR-GHRH antagonists were synthesized using the Fmoc peptide synthesis on [3-((Methyl-Fmoc-amino)-methyl)indol-1-yl] acetyl AM resin or [3-{ethyl-Fmoc-amino)-methyl)indol-1-yl]acetyl AM resin. Before starting the synthesis, the Fmoc group was removed from the resin with 20% piperidine in DMF for 20 min. The side chain of Fmoc-amino acids were protected with acid unstable groups such as β-tert-Butyl ester for ASP, tert-Butyl(But) for Ser, Thr and Tyr; Pentamethyldihydrobenzofuran-5-sulfonyl(Pbf) for Har, DArg, Arg; N β-tert-Butoxycarbonyl (Boc) for Orn; N β-trityl for Asn; N β-trityl for Gln. N P-trityl for Lys and Nim-trityl for His; The coupling was performed by using 3 equivalents of Fmoc amino acid and [2-(1H-Benzotriazole-1-yl)-1,1,3,3-tetramethyluronium hexafluorophosphate](HBTU) mixed in the 0.5 M 1-Hydroxybenzotriazole (HOBT) DMF solution, followed by addition of 6 equivalents of N,N-Diisopropylethylamine (DIPEA) and stirred for a few minutes to become a complete solution, then immediately added to the resin and shaken for 1-2 hours to finish the coupling reaction. The resin with washing and deprotection of Fmoc group was continued for next coupling with following Fmoc acid.

Exemplary Synthesis of AVR-235

The following Fmoc amino acid were coupled in the indicated order on methylamide resin: Fmoc-Har(pbf), Fmoc-DArg(pbf), Fmoc-Nle, Fmoc-Ile, Fmoc-Asp(oBut), Fmoc-Gln(Trt), Fmoc-Leu, Fmoc-Leu, Fmoc-Lys(Boc), Fmoc-Arg(pbf), Fmoc-Ala, Fmoc-Ser(But), Fmoc-Leu, Fmoc-Gln(Trt), Fmoc-Abu, Fmoc-Leu, Fmoc-Val, Fmoc-Lys(Boc), Fmoc-Arg(pbf), Fmoc-Tyr(Me), Fmoc-Har(pbf), Fmoc-Ala, Fmoc-Thr(But), Fmoc-5FPhe, Fmoc-Ile, Fmoc-Ala, Fmoc-Asp(oBut), Fmoc-DArg(pbf), Fmoc-Tyr(But), Fmoc-Ada and 5FPhAc to obtain the protected resin 5FPhAc-Ada-Tyr(But)-DArg(pbf)-Asp(oBut)-Ala-Ile-5FPhe-Thr(But)-Ala-Har(pbf)-Tyr(Me)-Arg(pbf)-Lys(Boc)-Val-Leu-Abu-Gln(Trt)-Leu-Ser(But)-Ala-Arg(pbf)-Lys(Boc)-Leu-Leu-Gln(Trt)-Asp(oBut)-Ile-Nle-DArg(pbf)-Har(pbf)-NHCH3-(R) (SEQ ID NO: 25). The protected peptide resin was treated with a mixed reagent and scavengers containing TFA/thioanisol/1,2-Ethanedithiol (EDT)/Anisol/H2O/Phenol (85%/5%/3%/2%/3%/2% by volume) at room temperature for 3 hr. The crude peptide was precipitated with tert-butyl methyl ether and purified with HPLC and analyzed by mass spectrometry.

The purification of the crude peptides was performed on a Beckman Gold HPLC System (Beckman Coulter, Inc., Brea, CA) equipped with 127P solvent Module, model 166P UVVIS Detector, using an XBridge™ reversed phase column (10 mm×250 mm), packed with C18 silica gel, 300 Å pore size, 5 m particle size (Waters Co., Milford, MA). The peptides were eluted with a solvent system consisting of solvent A (0.1% aqueous TFA) and solvent B (0.1% TFA in 70% aqueous acetonitrile (MeCN)) in a linear gradient mode of 30-55% of solvent B for 120 min at a flow rate of 5 ml/min. The eluent was monitored at 220 and 280 nm, and the fractions were examined by analytical HPLC using a Hewlett-Packard Model HP-1090 liquid chromatograph and pooled to give maximum purity. Analytical HPLC was carried out on a Supelco Discovery HS C18 reversed-phase column (2.1 mm×50 mm, C18, 300 Å pore size, 3 m particle size; Supelco Bellefonte, PA) using gradient elution from 40 to 80% B for 40 min with a solvent system consisting of solvents A and B, defined above, with a flow rate of 0.2 ml/min. The peaks were monitored at 220 and 280 nm. The peptides were judged to be substantially (>95%) pure by analytical HPLC. Molecular masses were determined by Agilent 6210 time-of-flight mass spectrometry in conjugation with 1200 CapLC (Agilent Technologies 6210 Time-of Light LC/MS, Santa Clara, CA). Peptides were eluted on an Agilent Zorbax C18 column (0.5 mm×150 mm, 300 Å pore size, 5 m particle size, Agilent, Santa Clara, CA) at a flow rate of 15 l/min with a linear gradient from 35 to 85% B for 30 min. Solvent A is 0.1% formic acid (FA), Solvent B is 90% aqueous MeCN/0.1% FA. TOF settings are as follow: capillary voltage: 4000V; drying gas flow: 7 L/min; drying gas temperature: 300° C.; nebulizer gas: 30 psi; fragmentor voltage: 350V.

Exemplary Synthesis of AVR-354

The following Fmoc amino acid were coupled in indicated order on the [3-((Methyl-Fmoc-amino)-methyl)indol-1-yl]acetyl AM resin Fmoc-Ada, Fmoc-Har(pbf), Fmoc-DArg(pbf), Fmoc-Nle, Fmoc-Ile, Fmoc-Asp(oBut), Fmoc-Gln(Trt), Fmoc-Leu, Fmoc-Leu, Fmoc-Lys(Boc), Fmoc-Arg(pbf), Fmoc-Ala, Fmoc-Ser(But), Fmoc-Leu, Fmoc-Gln(Trt), Fmoc-Abu, Fmoc-Leu, Fmoc-Val, Fmoc-Lys(Boc), Fmoc-Arg(pbf), Fmoc-5FPhe, Fmoc-Har(pbf), Fmoc-Ala, Fmoc-Thr(But), Fmoc-Cpa, Fmoc-Ile, Fmoc-Ala, Fmoc-Asp(oBut), Fmoc-DArg(pbf), Fmoc-Tyr(But), Fmoc-Ada and 5FPhAc.

Synthesis of C-terminal amide compounds of AVR 333, AVR 352 and AVR353

AVR-333, AVR-352 and AVR-353 were synthesized on Rink amide MBHA resin with Fmoc synthesis procedure as described in the synthesis of AVR-235.

For the synthesis of AVR-333, the following Fmoc amid acids were coupled in indicated order on the resin: Fmoc-Ada, Fmoc-Har(pbf), Fmoc-DArg(pbf), Fmoc-Nle, Fmoc-Ile, Fmoc-Asp(oBut), Fmoc-Gln(Trt), Fmoc-Leu, Fmoc-Leu, Fmoc-Lys(Boc), Fmoc-Arg(pbf), Fmoc-Ala, Fmoc-Ser(But), Fmoc-Leu, Fmoc-Gln(Trt), Fmoc-Abu, Fmoc-Leu, Fmoc-Val, Fmoc-Lys(Boc), Fmoc-Arg(pbf), Fmoc-Tyr(Me), Fmoc-Har(pbf), Fmoc-Asn(Trt), Fmoc-Thr(But), Fmoc-Cpa, Fmoc-Ile, Fmoc-Ala, Fmoc-Asp(oBut), Fmoc-DArg(pbf), Fmoc-Tyr(But), Fmoc-Ada and 5FPhAc.

For the synthesis of AVR 352, the following Fmoc amino acids were coupled in indicated order on Rink amide MBHA resin: Fmoc-Ada, Fmoc-Har(pbf), Fmoc-DArg(pbf), Fmoc-Nle, Fmoc-Ile, Fmoc-Asp(oBut), Fmoc-Gln(Trt), Fmoc-Leu, Fmoc-Leu, Fmoc-Lys(Boc), Fmoc-Arg(pbf), Fmoc-Ala, Fmoc-Ser(But), Fmoc-Leu, Fmoc-Gln(Trt), Fmoc-Abu, Fmoc-Leu, Fmoc-Val, Fmoc-Lys(Boc), Fmoc-Arg(pbf), Fmoc-5FPhe, Fmoc-Har(pbf), Fmoc-Ala, Fmoc-Thr(But), Fmoc-5FPhe, Fmoc-Ile, Fmoc-Ala, Fmoc-Asp(oBut), Fmoc-DArg(pbf), Fmoc-Tyr(But), Fmoc-Ada and 5FPhAc.

For the synthesis of AVR-353, the following Fmoc amino acids were coupled in indicated order on Rink amide MBHA resin: Fmoc-Ada, Fmoc-Har(pbf), Fmoc-DArg(pbf), Fmoc-Nle, Fmoc-Ile, Fmoc-Asp(oBut), Fmoc-Gln(Trt), Fmoc-Leu, Fmoc-Leu, Fmoc-Lys(Boc), Fmoc-Arg(pbf), Fmoc- Ala, Fmoc-Ser(But), Fmoc-Leu, Fmoc-Gln(Trt), Fmoc-Abu, Fmoc-Leu, Fmoc-Val, Fmoc-Lys(Boc), Fmoc-Arg (pbf), Fmoc-5FPhe, Fmoc-Har(pbf), Fmoc-Ala, Fmoc-Thr (But), Fmoc-Cpa, Fmoc-Ile, Fmoc-Ala, Fmoc-Asp(oBut), Fmoc-DArg(pbf), Fmoc-Tyr(But), Fmoc-Ada and 5FPhAc.

As shown in FIG. 8, certain AVR compounds have 5PhAc at N-terminal, Arg at positions 2 and 20, Lys at positions 12 and 21, and modified C-terminal $NH_2$ with —$NHCH_3$ (AVR-235), Ada-$NH_2$ (AVR-353 and AVR-352), or -Ada-NHCH3 (AVR-354).

REFERENCES

1. Mirsaeidi M, Machado R F, Schraufnagel D, Sweiss N J, Baughman R P. Racial difference in sarcoidosis mortality in the United States. *Chest.* 2015; 147(2):438-449.
2. Chen E S, Moller D R. Etiology of sarcoidosis. *Clinics in chest medicine.* 2008; 29(3):365-377, vii.
3. Koh T J, DiPietro L A. Inflammation and wound healing: the role of the macrophage. *Expert Rev Mol Med.* 2011; 13:e23.
4. Patterson K C, Strek M E. Pulmonary fibrosis in sarcoidosis. Clinical features and outcomes. *Annals of the American Thoracic Society.* 2013; 10(4):362-370.
5. Baughman R P, Teirstein A S, Judson M A, et al. Clinical characteristics of patients in a case control study of sarcoidosis. *Am J Respir Crit Care Med.* 2001; 164(10 Pt 1):1885-1889.
6. Miller M A, Bass H E. Effect of Acthar-c (ACTH) in sarcoidosis. *Ann Intern Med.* 1952; 37(4):776-784.
7. Baughman R P, Barney J B, O'Hare L, Lower E E. A retrospective pilot study examining the use of Acthar gel in sarcoidosis patients. *Respir Med.* 2016; 110:66-72.
8. Lazarus A. Sarcoidosis: epidemiology, etiology, pathogenesis, and genetics. *Dis Mon.* 2009; 55(11):649-660.
9. Nunes H, Bouvry D, Soler P, Valeyre D. Sarcoidosis. *Orphanet J Rare Dis.* 2007; 2:46.
10. Centers for Disease Control and Prevention N CfHS. Underlying Cause of Death 1999-2010 on CDC WONDER Online Database, released 2012. *Data are from the Multiple Cause of Death Files,* 1999-2010, as compiled from data provided by the 57 vital statistics jurisdictions through the Vital Statistics Cooperative Program. Accessed at http://wonder.cdc.gov/ucd-icd10.html Jul. 17, 2013.
11. Iannuzzi M C, Rybicki B A, Teirstein A S. Sarcoidosis. N Engl *J Med.* 2007; 357(21):2153-2165.
12. Newman L S, Rose C S, Bresnitz E A, et al. A case control etiologic study of sarcoidosis: environmental and occupational risk factors. *American journal of respiratory and critical care medicine.* 2004; 170(12):1324-1330.
13. Kucera G P, Rybicki B A, Kirkey K L, et al. Occupational risk factors for sarcoidosis in African-American siblings. *Chest.* 2003; 123(5):1527-1535.
14. Dubaniewicz A, Dubaniewicz-Wybieralska M, Sternau A, et al. *Mycobacterium tuberculosis* complex and mycobacterial heat shock proteins in lymph node tissue from patients with pulmonary sarcoidosis. *J Clin Microbiol.* 2006; 44(9):3448-3451.
15. Chen E S, Song Z, Willett M H, et al. Serum amyloid A regulates granulomatous inflammation in sarcoidosis through Toll-like receptor-2. *American journal of respiratory and critical care medicine.* 2010; 181(4):360-373.
16. Oswald-Richter K A, Beachboard D C, Seeley E H, et al. Dual analysis for mycobacteria and propionibacteria in sarcoidosis BAL. *J Clin Immunol.* 2012; 32(5):1129-1140.
17. Fang C, Huang H, Xu Z. Immunological Evidence for the Role of Mycobacteria in Sarcoidosis: A Meta-Analysis. *PLoS One.* 2016; 11(8):e0154716.
18. Brownell I, Ramirez-Valle F, Sanchez M, Prystowsky S. Evidence for mycobacteria in sarcoidosis. *Am J Respir Cell Mol Biol.* 2011; 45(5):899-905.
19. Rutherford R M, Gilmartin J J. Mycobacteria in pathogenesis of sarcoidosis. *Chest.* 2004; 125(1):354.

What is claimed is:

1. A method of treating pulmonary sarcoidosis in a subject, the method comprising administering to the subject a therapeutically effective amount of a peptide comprising the amino acid sequence (a)
(AVR-235, SEQ ID NO: 3)
5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-$NHCH_3$;

(b)
(AVR-333, SEQ ID NO: 4)
5FPhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-$NH_2$;

(c)
(AVR-352, SEQ ID NO: 5)
5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-$NH_2$;

(d)
(AVR-353, SEQ ID NO: 6)
5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-$NH_2$;

(e)
(AVR-354, SEQ ID NO: 7)
5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-$NHCH_3$;

(f)
(AVR-104, SEQ ID NO: 8)
PhAC-Ada-Tyr-DArg-Asp-Ala-Ile-Cpa-Thr-Ala-Arg-Tyr(Me)-Arg-Lys-Val-Leu-Abu-Gln-Leu-Ser-Ala-His-Orn-Leu-Leu-Gln-Asp-Ile-Nle-DArg-Har-$NH_2$;

(g)
(AVR-107, SEQ ID NO: 9)
PhAC-Ada-Tyr-DArg-Asp-Ala-Ile-Cpa-Thr-Ala-Arg-Tyr-Arg-Lys-Val-Leu-Abu-Gln-Leu-Ser-Ala-Arg-Lys-Leu-Leu-Gln-Asp-Ile-Nle-DArg-Har-$NH_2$;

(h)
(AVR-116, SEQ ID NO: 10)
PhAC-Ada-Tyr-DArg-Asp-Ala-Ile-Cpa-Thr-Ala-Arg-5FPhe-Arg-Lys-Val-Leu-Abu-Gln-Leu-Ser-Ala-His-Orn-Leu-Leu-Gln-Asp-Ile-Nle-DArg-Har-$NH_2$;

(i)
(AVR-120, SEQ ID NO: 11)
D-Phe-Ada-Tyr-DArg-Asp-Ala-Ile-Cpa-Thr-Ala-Arg-Tyr(Me)-Arg-Lys-Val-Leu-Abu-Gln-Leu-Ser-Ala-His-Orn-Leu-Leu-Gln-Asp-Ile-Nle-DArg-Har-$NH_2$;

-continued (j)
(AVR-201, SEQ ID NO: 12)
PhAC-Ada-Tyr-DArg-Asp-Ala-Ile-Cpa-Thr-Ala-Arg-Amp-Arg-Lys-Val-Leu-Abu-Gln-Leu-Ser-Ala-His-Orn-Leu-Leu-Gln-Asp-Ile-Nle-DArg-Har-$NHCH_3$;

(j)
(AVR-234, SEQ ID NO: 13)
PhAC-Ada-Tyr-DArg-Asp-Ala-Ile-Cpa-Thr-Asn-Arg-Tyr(Me)-Arg-Lys-Val-Leu-Abu-Gln-Leu-Ser-Ala-Arg-Lys-Leu-Leu-Gln-Asp-Ile-Nle-DArg-Har-$NHCH_3$;

(k)
(AVR-321, SEQ ID NO: 14)
PhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Aoc-$NHCH_3$;

(l)
(AVR-322, SEQ ID NO: 15)
5FPhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Aoc-$NHCH_3$;

(m)
(AVR-542, SEQ ID NO: 26)
5FPhAC-Ada-Tyr-DArg-Asp-Ala-Ile-Cpa-Thr-Ala-Har-5FPhe-His-Orn-Val-Leu-Abu-Gln-Leu-Ser-Ala-His-Orn-Leu-Leu-Gln-Asp-Ile-Nle-DArg-Har-$NHCH_3$;

(n)
(AVR-543, SEQ ID NO: 17)
5FPhAC-Ada-Tyr-DArg-Asp-Ala-Ile-Cpa-Thr-Ala-Har-5FPhe-His-Orn-Val-Leu-Abu-Gln-Leu-Ser-Ala-His-Orn-Leu-Leu-Gln-Asp-Ile-Nle-DArg-Har-Ada-$NHCH_3$;

(o)
(AVR-552, SEQ ID NO: 18)
5FPhAC-Ada-Tyr-DArg-Asp-Ala-Ile-Cpa-Thr-Ala-Har-5FPhe-His-Orn-Val-Leu-Abu-Gln-Leu-Ser-Ala-His-Orn-Leu-Leu-Gln-Asp-Ile-Nle-DArg-Har-Ada-$NH_2$;

(p)
(AVR-553, SEQ ID NO: 19)
5FPhAC-Ada-Tyr-DArg-Asp-Ala-Ile-5FPhe-Thr-Ala-Har-Tyr(Me)-His-Orn-Val-Leu-Abu-Gln-Leu-Ser-Ala-His-Orn-Leu-Leu-Gln-Asp-Ile-Nle-DArg-Har-Ada-$NH_2$;
or (q)
(AVR-620, SEQ ID NO: 20)
5FPhAC-Ada-Tyr-DArg-Asp-Ala-Ile-Cpa-Thr-Asn-Arg-Tyr(Me)-Arg-Lys-Val-Leu-Abu-Gln-Leu-Ser-Ala-His-Orn-Leu-Leu-Gln-Asp-Ile-Nle-DArg-Har-Ada-$NH_2$.

2. The method of claim 1, wherein the peptide comprises the amino acid sequence (a)

(AVR-235, SEQ ID NO: 3)

5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-$NHCH_3$;

(b)

(AVR-333, SEQ ID NO: 4)

5FPhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-$NH_2$;

(c)

(AVR-352, SEQ ID NO: 5)

5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-$NH_2$;

(d)

(AVR-353, SEQ ID NO: 6)

5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-$NH_2$;

or (e)

(AVR-354, SEQ ID NO: 7)

5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-$NHCH_3$.

3. The method of claim 1, wherein the peptide or pharmaceutically acceptable salt thereof is administered via intranasal, inhalation, intrapulmonary, intra-airway, intrabronchial, or intratracheal delivery.

* * * * *